(12) United States Patent
Bennett et al.

(10) Patent No.: US 7,562,557 B2
(45) Date of Patent: Jul. 21, 2009

(54) FLEXURAL RESONATOR SENSING DEVICE AND METHOD

(75) Inventors: James Bennett, Santa Clara, CA (US); Oleg Kolosov, San Jose, CA (US); Leonid Matsiev, San Jose, CA (US)

(73) Assignee: MEAS France, Toulouse (FR)

( * ) Notice: Subject to any disclaimer, the term of this patent is extended or adjusted under 35 U.S.C. 154(b) by 192 days.

(21) Appl. No.: 11/111,165

(22) Filed: Apr. 20, 2005

(65) Prior Publication Data

US 2005/0262944 A1 Dec. 1, 2005

Related U.S. Application Data

(60) Provisional application No. 60/564,562, filed on Apr. 21, 2004.

(51) Int. Cl.
*G01N 29/036* (2006.01)
*G01N 29/24* (2006.01)
*H01L 41/047* (2006.01)

(52) U.S. Cl. .............. 73/24.06; 73/32 A; 73/64.53; 73/579; 310/320; 310/321; 310/365; 310/366; 310/370

(58) Field of Classification Search .................. 73/579
See application file for complete search history.

(56) References Cited

U.S. PATENT DOCUMENTS

| 4,302,694 | A |  | 11/1981 | Fujishima |  |
|---|---|---|---|---|---|
| 4,558,248 | A |  | 12/1985 | Valentin |  |
| 4,652,784 | A |  | 3/1987 | Inoue |  |
| 4,900,970 | A | * | 2/1990 | Ando et al. | 310/320 |
| 4,922,745 | A | * | 5/1990 | Rudkin et al. | 73/32 A |
| 5,225,731 | A | * | 7/1993 | Owen | 310/366 |
| 5,357,108 | A | * | 10/1994 | Suzuki et al. | 250/306 |
| 5,506,829 | A | * | 4/1996 | Yagi et al. | 369/126 |
| 5,852,229 | A |  | 12/1998 | Josse |  |
| 5,914,556 | A |  | 6/1999 | Tabota |  |
| 5,920,972 | A |  | 7/1999 | Palczewska |  |
| 5,936,150 | A |  | 8/1999 | Kobrin |  |
| 6,040,652 | A | * | 3/2000 | Kaida | 310/320 |
| 6,494,079 | B1 |  | 12/2002 | Matsiev |  |
| 6,700,302 | B1 |  | 3/2004 | Yamamoto |  |
| 6,940,213 | B1 |  | 9/2005 | Heinz |  |
| 7,210,332 | B2 | * | 5/2007 | Kolosov et al. | 73/24.06 |

FOREIGN PATENT DOCUMENTS

DE 10308975 A1 2/2004
WO WO 03/052350 A1 * 6/2003

OTHER PUBLICATIONS

International Search Report for PCT/US2005/013643 dated Feb. 8, 2006, 2 pgs.

* cited by examiner

*Primary Examiner*—Hezron Williams
*Assistant Examiner*—Rose M Miller
(74) *Attorney, Agent, or Firm*—Senniger Powers LLP

(57) ABSTRACT

A flexural resonator includes a piezoelectric material. At least a portion of an electrode having a first surface and a second surface is embedded in the piezoelectric material such that the piezoelectric material is disposed over and in electronic association with the first and second surfaces of the electrode.

29 Claims, 19 Drawing Sheets

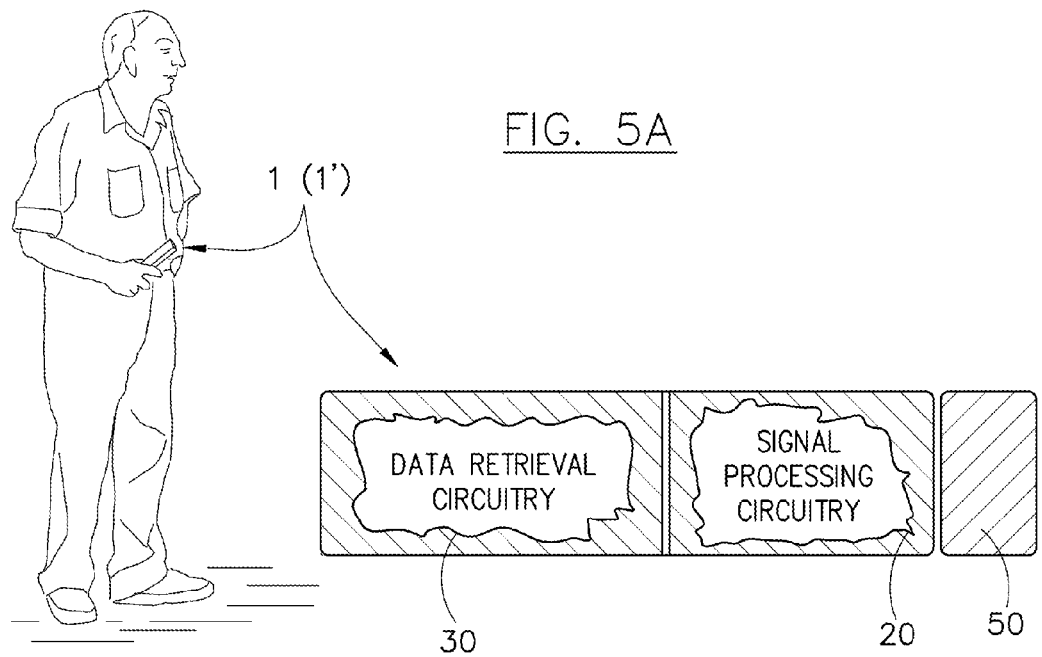
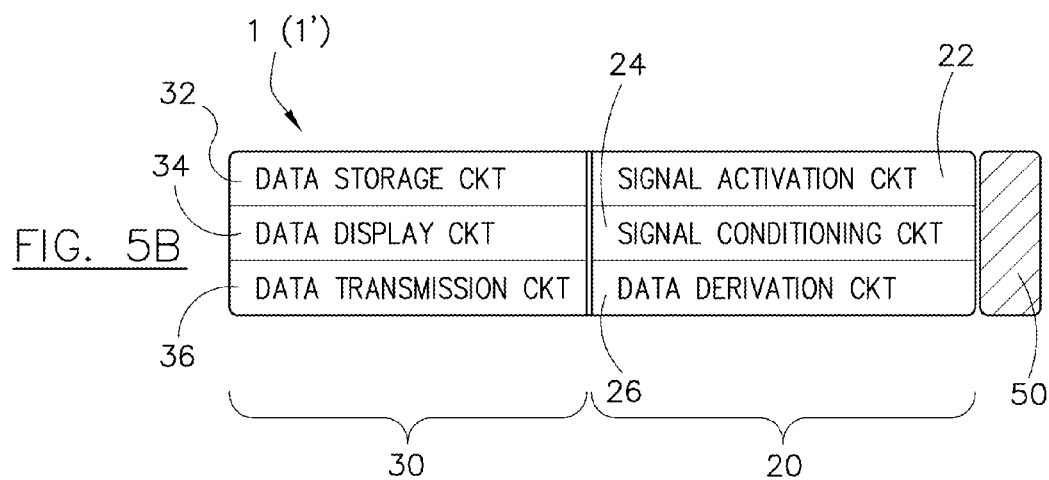
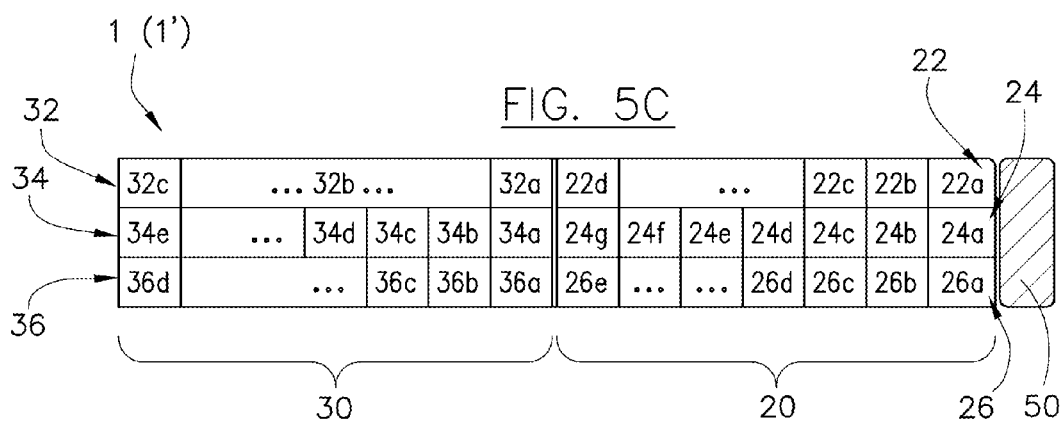

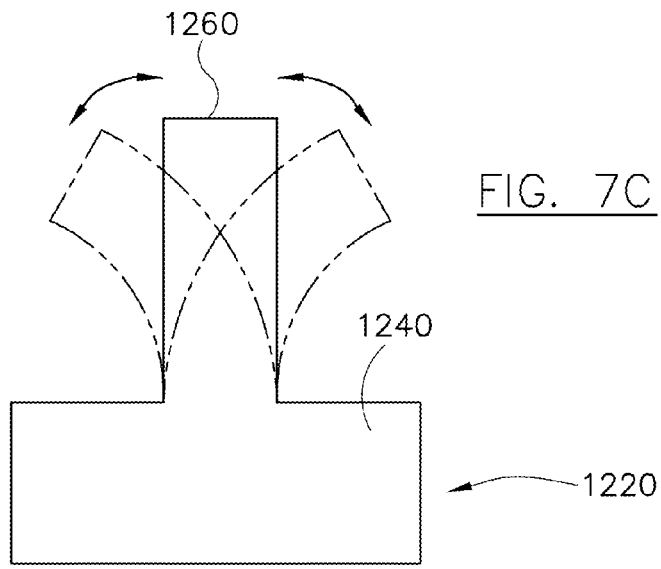
FIG. 7C
FIG. 7D
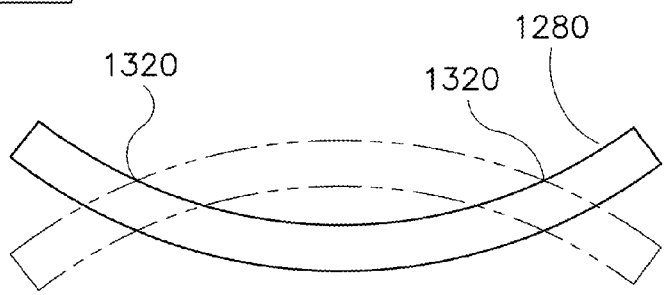
FIG. 7E
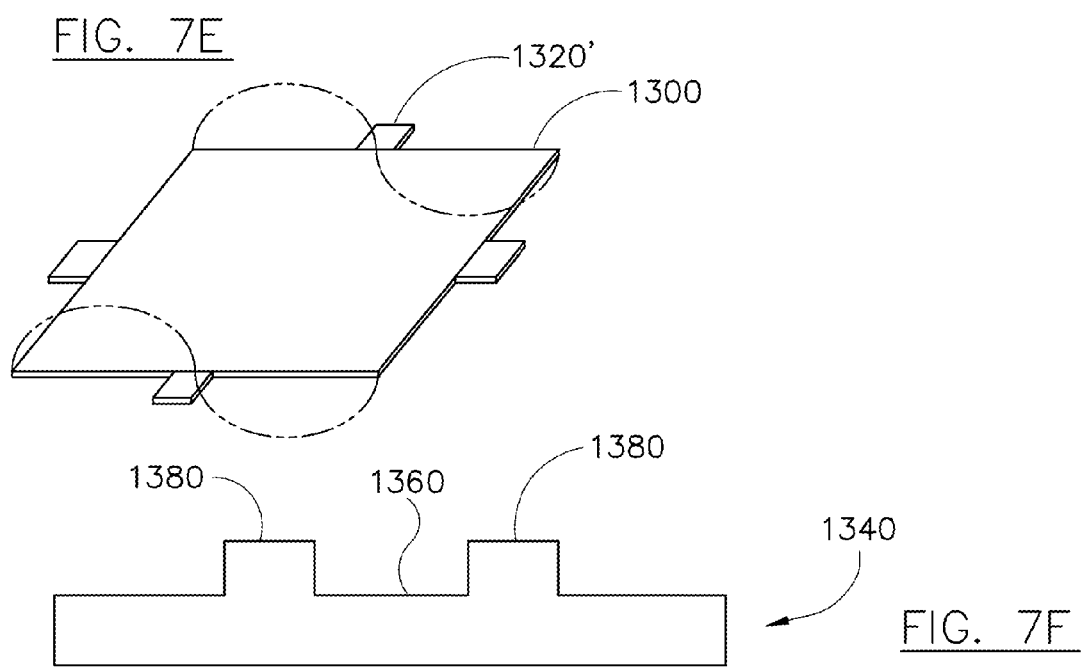
FIG. 7F

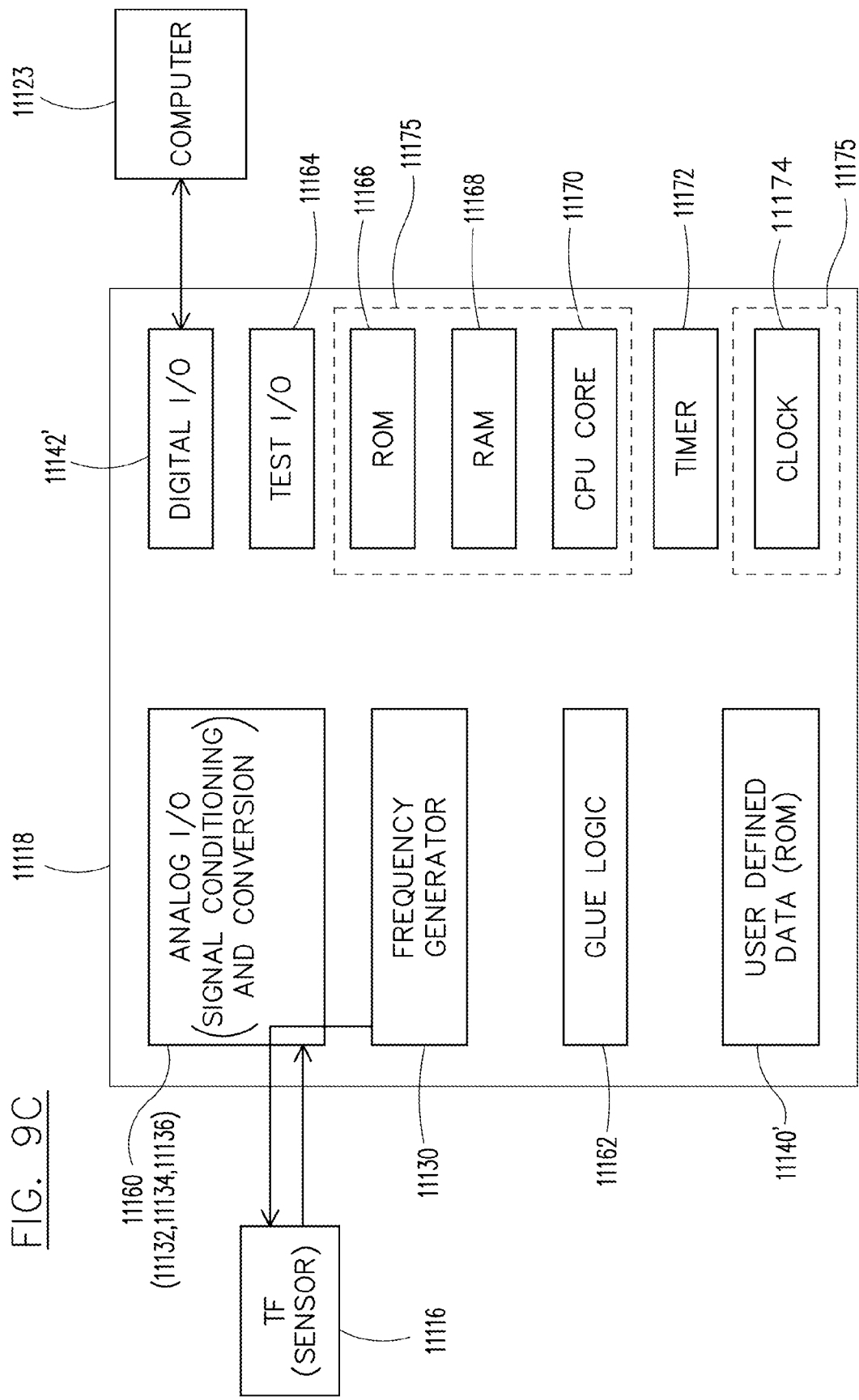

FIG. 9D

APPROXIMATED FLUID CHARACTERISTICS

| | | DENSITY | VISCOSITY | DIELECTRIC CONSTANT |
|---|---|---|---|---|
| TUNING FORK 1.1 TEMP. 25°C | OIL TYPE 1 | $\rho$ | $\eta$ | $\varepsilon$ |
| | OIL TYPE 2 | $\rho$ | $\eta$ | $\varepsilon$ |
| | OIL TYPE 3 | $\rho$ | $\eta$ | $\varepsilon$ |
| CALIBRATION VARIABLES $V_1$ $V_2$ $V_3$ $V_4$ $V_5$ $V_6$ $V_7$ | OIL TYPE 4 | $\rho$ | $\eta$ | $\varepsilon$ |
| | OIL TYPE 5 | $\rho$ | $\eta$ | $\varepsilon$ |
| | OIL TYPE 6 | $\rho$ | $\eta$ | $\varepsilon$ |
| | ⋮ | ⋮ | ⋮ | ⋮ |
| | OIL TYPE N | $\rho$ | $\eta$ | $\varepsilon$ |

FIG. 9E

APPROXIMATED FLUID CHARACTERISTICS

| | | DENSITY | VISCOSITY | DIELECTRIC CONSTANT |
|---|---|---|---|---|
| TUNING FORK 1.1 TEMP. 40°C | OIL TYPE 1 | $\rho'$ | $\eta'$ | $\varepsilon'$ |
| | OIL TYPE 2 | $\rho'$ | $\eta'$ | $\varepsilon'$ |
| | OIL TYPE 3 | $\rho'$ | $\eta'$ | $\varepsilon'$ |
| CALIBRATION VARIABLES $V_1'$ $V_2'$ $V_3'$ $V_4'$ $V_5'$ $V_6'$ $V_7'$ | OIL TYPE 4 | $\rho'$ | $\eta'$ | $\varepsilon'$ |
| | OIL TYPE 5 | $\rho'$ | $\eta'$ | $\varepsilon'$ |
| | OIL TYPE 6 | $\rho'$ | $\eta'$ | $\varepsilon'$ |
| | ⋮ | ⋮ | ⋮ | ⋮ |
| | OIL TYPE N | $\rho'$ | $\eta'$ | $\varepsilon'$ |

FLEXURAL RESONATOR SENSING DEVICE AND METHOD

BACKGROUND OF INVENTION

The present invention generally relates to the field of fluid sensors and more particularly to the field of portable fluid sensor devices and methods useful in field operations, including field operations involving process monitoring, process control and/or process or system servicing. The present invention relates, in preferred embodiments, to portable fluid sensor devices and methods adapted for use in closed fluid systems such as recirculating fluid systems (e.g., environmental control systems, engine systems, transportation vehicle systems, etc.). The present invention relates, in particularly preferred embodiments, to the field of fluid sensor devices and methods involving a mechanical resonator sensor such as a flexural resonator sensor.

Effective approaches for measuring characteristics of fluids using mechanical resonators are disclosed in commonly-owned U.S. Pat. Nos. 6,401,519; 6,393,895; 6,336,353; 6,182,499; and 6,494,079, each of which are incorporated by reference herein for all purposes. See also, Matsiev, "Application of Flexural Mechanical Resonators to Simultaneous Measurements of Liquid Density and Viscosity," IEEE International Ultrasonics Symposium, Oct. 17-20, 1999, Lake Tahoe, Nev. and EP 0943091 B1. The use of a quartz oscillator in a sensor has been described as well in U.S. Pat. Nos. 6,223,589 and 5,741,961, and in Hammond, et al., "An Acoustic Automotive Engine Oil Quality Sensor", Proceedings of the 1997 IEEE International Frequency Control Symposium, IEEE Catalog No. 97CH36016, pp. 72-80, May 28-30, 1997.

The use of other types of sensors is also known in the art. For example, the use of acoustic sensors has been addressed in applications such as viscosity measurement in J. W. Grate, et al, Anal. Chem. 65, 940A-948A (1993)); *"Viscosity and Density Sensing with Ultrasonic Plate Waves"*, B. A. Martin, S. W. Wenzel, and R. M. White, Sensors and Actuators, A21-A23 (1990), 704-708; *"Preparation of chemically etched piezoelectric resonators for density meters and viscometers"*, S. Trolier, Q. C. Xu, R. E. Newnham, Mat. Res. Bull. 22, 1267-74 (1987); *"On-line Sensor for Density and Viscosity Measurement of a Liquid or Slurry for Process Control in the Food Industry"*, Margaret S. Greenwood, Ph.D. James R. Skorpik, Judith Ann Bamberger, P. E. Sixth Conference on Food Engineering, 1999 AIChE Annual Meeting, Dallas, Tex.; U.S. Pat. Nos. 5,708,191; 5,886,250; 6,082,180; 6,082,181; and 6,311,549; and *"Micromachined viscosity sensor for real-time polymerization monitoring."*, O. Brand, J. M. English, S. A. Bidstrup, M. G. Allen, Transducers '97, 121-124 (1997). See also, U.S. Pat. No. 5,586,445 (*"Low Refrigerant Charge Detection Using a Combined Pressure/Temperature Sensor"*).

Notwithstanding the above, there remains a need in the art for alternative or improved sensor devices and methods for efficiently evaluating fluids used in fluidic systems, including for example in residential, commercial and industrial process streams and/or in machines used in such process streams and/or in stand-alone machines. Examples in which such a need exists include those fluidic systems used in connection with the petroleum, chemical, pharmaceutical, healthcare, environmental, military, aerospace, construction, heating, ventilating, air-conditioning, refrigeration, food, and transportation industries. In particular, there remains a need in the art for a cost-effective, more universal flexural resonator sensing element that can be employed across a wide variety of fluids, including for example ionic fluids.

SUMMARY OF INVENTION

It is therefore an object of the present invention to provide improved sensor devices and methods for efficiently monitoring fluids used in fluidic systems. In particular, it is an object of the invention to provide a cost-effective, more universal flexural resonator sensor element suitable for employment across a variety of fluids, including ionic fluids.

Briefly, therefore, the present invention is broadly directed to various methods for monitoring a property of a fluid in a fluidic system using a sensor, such as a mechanical resonator sensor, preferably having a mechanical resonator sensing element comprising one or more embedded electrodes. In preferred embodiments, the sensor is a flexural resonator sensor comprising a flexural resonator sensing element having one or more embedded electrodes.

The invention is also broadly directed to a system for monitoring a property of one or more fluids in one or more fluidic systems, and in preferred embodiments, in multiple fluidic systems. The system generally comprises a sensor comprising a mechanical resonator sensing element, such as a flexural resonator sensing element. The sensing element preferably comprises one or more embedded electrodes, and preferably comprises a sensing surface for contacting a fluid. The system also comprises one or more circuits, such as signal processing circuits and/or data retrieval circuits in electrical communication with the sensing element.

The invention is further broadly directed to an apparatus for use in monitoring a property of one or more fluids in one or more fluidic systems. Such apparatus generally comprises a mechanical resonator sensing element, preferably a flexural resonator sensing element. The sensing element comprises one or more embedded electrodes.

In the methods, systems and apparatus of the present invention, a sensing element comprises an embedded electrode, and in operation, further comprises a sensing surface for contacting a fluid during a sensing period. The sensing element is more particularly characterized in the following paragraphs, and the subsequent discussion.

Generally, in a first embodiment, the apparatus comprises a flexural resonator or a torsional resonator, the flexural resonator or a torsional resonator comprising a piezoelectric material, and an electrode comprising at least a first surface and a second surface. At least a portion of the electrode is embedded in the piezoelectric material such that the piezoelectric material is disposed over and in electronic association with the first surface of the electrode, and such that the piezoelectric material is disposed over and in electronic association with the second surface of the electrode.

In a second general embodiment, the apparatus comprises a flexural resonator or a torsional resonator, preferably adaptable for determining a property of a fluid, the flexural resonator or torsional resonator comprising a sensing portion having an exposed surface for contacting the fluid, a piezoelectric material, and at a least one pair of electrodes configured for generating an electric field between the electrodes and within the piezoelectric material. The at least one pair of electrodes comprises a first electrode, at least a portion of the first electrode having a surface in electronic association with the piezoelectric material, and a second electrode, at least a portion of the second electrode having a first surface and a second surface, the first surface thereof being in electronic association with the piezoelectric material, the second surface thereof being configured such that the exposed surface of the sensing portion consists essentially of the second surface thereof.

In a third general embodiment, the apparatus comprises a flexural resonator or a torsional resonator, preferably adaptable for determining a property of a fluid, the flexural resonator or the torsional resonator comprising a sensing portion having an exposed surface for contacting the fluid, a piezoelectric material, and at a least one pair of electrodes configured for generating an electric field between the electrodes and within the piezoelectric material. The at least one pair of electrodes comprises a first electrode, at least a portion of the first electrode having a surface in electronic association with the piezoelectric material, and a second electrode, at least a portion of the second electrode having a first surface in electronic association with the piezoelectric material. The first and second electrodes are configured such that upon activation, the electric field generated between is substantially contained within the piezoelectric material. Preferably, upon activation, the piezoelectric material resonates.

In a fourth general embodiment, the apparatus comprises a mechanical resonator, wherein the mechanical resonator is a flexural resonator or a torsional resonator. The mechanical resonator comprises a sensing portion having an exposed surface for contacting the fluid, and in particular, the sensing portion of the mechanical resonator includes at least one unrestrained end configured for sensing contact with the fluid. (For example, the resonator can be a flexural resonator such as a tuning fork having two or more tines, each of the tines having an unrestrained end configured for contacting the fluid; alternatively for example, the resonator can be a cantilever having one unrestrained end configured for contacting the fluid; or as another example, the resonator can be a torsional resonator having one unrestrained end configured for contacting the fluid. Regardless of the particular design, the mechanical resonator can further comprise a piezoelectric material, and at a least one pair of electrodes configured for generating an electric field between them within the piezoelectric material, the at least one pair of electrodes comprising at least a first electrode, with at least a portion of the first electrode having at least one surface in electronic association with the piezoelectric material. The mechanical resonator of this embodiment also comprises an external second electrode comprising a conductive overlayer, covering over at least the sensing portion of the mechanical resonator, including the at least one unrestrained end thereof. Preferably, the exposed surface of the sensing portion consists essentially of an exposed surface the conductive overlayer.

In each of the aforementioned embodiments (e.g., each of the first, second, third and fourth embodiments of the apparatus, together with the corresponding embodiments for the methods and systems of the invention), the invention can include one or more of the following features, in various combinations and permutations: (i) the flexural resonator is preferably a tuning fork resonator; (ii) upon electronic activation, the piezoelectric material resonates at a frequency of not more than about 1 MHz; (iii) upon electronic activation, the piezoelectric material resonates such that the sensing surface of the flexural resonator displaces a fluid; and/or (iv) upon fluidic activation, the piezoelectric material is displaced by a fluid such that a detectable electrical signal is generated in one or more electrodes.

Further, in each of the aforementioned embodiments (e.g., each of the first, second, third and fourth embodiments of the apparatus, together with the corresponding embodiments for the methods and systems of the invention), the invention can include one or more of the following features, in various combinations and permutations: (i) the electrode(s) can comprise at least a first surface and a second surface; (ii) the second surface of the electrode(s) can be substantially geometrically opposed to the first surface of the electrode(s); (iii) the first surface of the electrode(s) can be a first major surface of the electrode(s), the second surface of the electrode(s) can be a second major surface of the electrode(s), with the first and second major surfaces being substantially parallel to and being substantially geometrically opposed to each other; and/or (iv) the electrode(s) can further comprise a third minor surface and a forth minor surface, with the third and forth minor surfaces being substantially parallel to and being substantially geometrically opposed to each other.

Further, in each of the aforementioned embodiments (e.g., each of the first, second, third and fourth embodiments of the apparatus, together with the corresponding embodiments for the methods and systems of the invention), the invention can include one or more of the following features, in various combinations and permutations, in particular in combination with an embodiment in which the first surface of the electrode(s) are a first major surface of the electrode(s), the second surface of the electrode(s) are a second major surface of the electrode(s), with the first and second major surfaces being substantially parallel to and being substantially geometrically opposed to each other, and in which the electrode(s) further comprise a third minor surface and a forth minor surface, with the third and forth minor surfaces being substantially parallel to and being substantially geometrically opposed to each other: (i) the piezoelectric material or at least one of the first piezoelectric material and the second piezoelectric material are disposed adjacent to and in electronic association with each of the third minor surface and the fourth minor surface of the electrode; (ii) the apparatus further comprises a bondable material disposed adjacent to and in contact with each of the third minor surface and the fourth minor surface of the electrode; and/or (iii) the apparatus further comprises an insulating material disposed adjacent to and in contact with each of the third minor surface and the fourth minor surface of the electrode.

Moreover, in each of the aforementioned embodiments (e.g., each of the first, second, third and fourth embodiments of the apparatus, together with the corresponding embodiments for the methods and systems of the invention), the invention can include one or more of the following features, in various combinations and permutations: (i) the flexural resonator comprises a sensing portion having an exposed surface for contacting a fluid, and the portion of the electrode embedded in the piezoelectric material corresponds at least to the sensing portion of the flexural resonator; and/or (ii) the entire operative electrode of the flexural resonator is embedded in the piezoelectric material.

Other objects and features will be in part apparent and in part pointed our hereinafter.

BRIEF DESCRIPTION OF THE DRAWINGS

FIGS. 5A through 5C are schematic representations of one embodiment of the invention involving a sensor (for example, a ported sensor) comprising signal processing circuitry and/or data retrieval circuitry.

FIGS. 7A through 7I are schematic representations of a fluidic system (FIG. 7A) and of several configurations for flexural resonator sensing elements (FIG. 7B through 7I).

FIGS. 9A through 9E are schematic representations of one preferred approach for circuitry that can be used in connection with embodiments of the invention, at least a portion of the circuitry being realized in an application specific integrated circuit (ASIC).

Figure 1A:
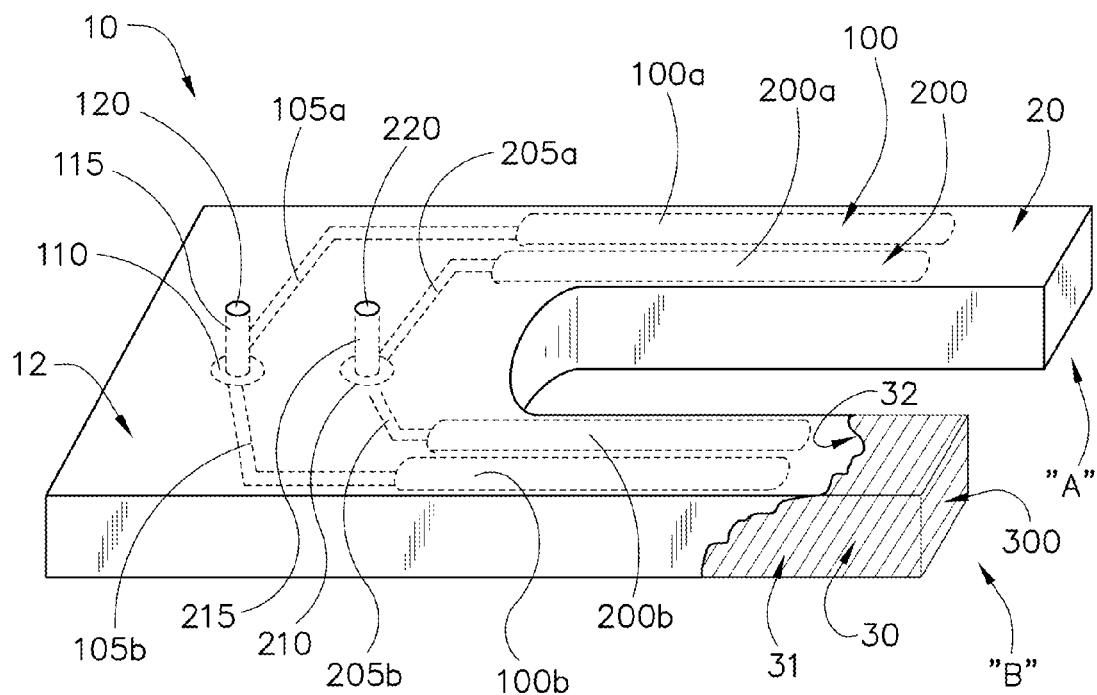
FIGS. 1A through 1C are schematic views of one embodiment of the invention involving a tuning fork resonator having two pairs of internal, embedded electrodes, including, including a schematic perspective view thereof (FIG. 1A), a tine-end end view thereof (FIG. 1B) and a top plan view of the electrode arrangement (FIG. 1C).

The invention is described in further detail below with reference to the figures, in which like items are numbered the same in the several figures.

DETAILED DESCRIPTION OF THE INVENTION

The following paragraphs describe certain features and combinations of features that can be used in connection with each of the methods, systems and apparatus of the invention, as generally described above. Also, particular features described hereinafter can be used in combination with other described features in each of the various possible combinations and permutations. Also, the invention is exemplified using tuning fork flexural resonators. However, the invention is not so limited, since the concepts employed in connection with the preferred tuning fork embodiment, while advantageous over other flexural resonator designs for many applications, can be applied as well to other types of flexural resonators, as described hereinafter. As such, the invention is not limited to the specifically described embodiments.

Preferred Apparatus

With reference to FIG. 1 (perspective view), the apparatus of the first general embodiment comprises a flexural resonator sensing element 10 (depicted in the FIG. 1 as a tuning fork, for example). The flexural resonator 10 comprises a piezoelectric material 20, and one or more electrodes, shown in the FIG. 1 as a first electrode 100 and a second electrode 200, each of which are embedded in the piezoelectric material 20. The first electrode 100 comprises a first portion 100a distributed within a first tine A of the tuning fork resonator 10 and a second portion 100b distributed over a second tine B of the tuning fork resonator 10. The first portion 100a and the second portion 100b of the first electrode 100 are each in electrical communication with a common first contact pad 110 through respective conductive paths (e.g., leads) 105a and 105b, and are therefore in common electrical communication with each other. Similarly, the second electrode 200 comprises a first portion 200a distributed within a first tine A of the tuning fork resonator 10 and a second portion 200b distributed over a second tine B of the tuning fork resonator 10. The first portion 200a and the second portion 200b of the second electrode 200 are each in electrical communication with a common second contact pad 210 through respective conductive paths (e.g., leads) 205a and 205b, and are therefore in common electrical communication with each other. A first electrical via 115 provides a conductive path between the common first contact pad 110 and a first external contact 120 on an external surface 12 of the flexural resonator 10. Similarly, a second electrical via 215 provides a conductive path between the common second contact pad 210 and a second external contact 220 on the external surface 12 of the flexural resonator 10.

Figure 1B:
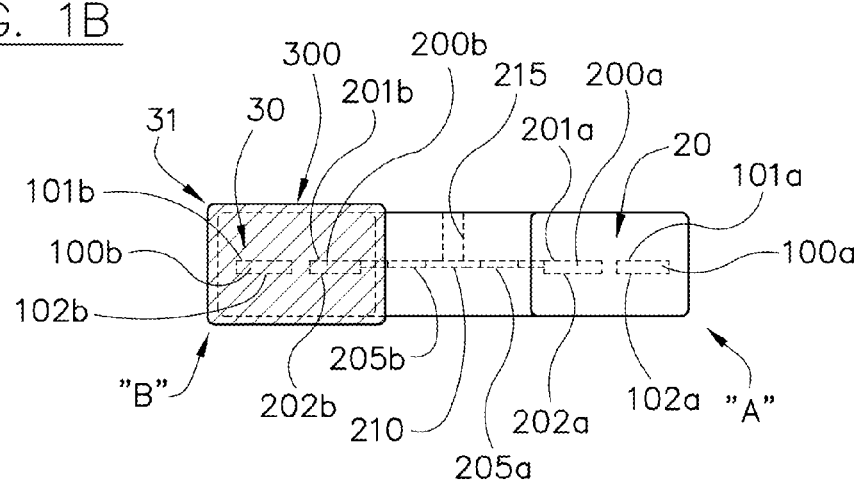

Referring now also to FIG. 1B (external end view looking from the tine ends of FIG. 1A), the first electrode 100 has a first surface (shown as a first surface 101a of the first portion 100a and a first surface 101b of the second portion 100b of the first electrode 100), and a second surface (shown as a second surface 102a of the first portion 100a and a second surface 102b of the second portion 100b of the first electrode 100). Similarly, the second electrode 200 has a first surface (shown as a first surface 201a of the first portion 200a and a first surface 201b of the second portion 200b of the second electrode 200), and a second surface (shown as a second surface 202a of the first portion 200a and a second surface 202b of the second portion 200b of the second electrode 200). Each of the first and second electrodes 100, 200 are embedded in the piezoelectric material 20, such that the piezoelectric material 20 is disposed over and in electronic association with the first surface of each of the first and second electrodes 100, 200, and such that the piezoelectric material is disposed over and in electronic association with the second surface of each of the first and second electrodes.

Referring to both FIGS. 1A and 1B, a sensing portion 15 of the flexural resonator 10 can have an exposed surface for contacting the fluid under test. The exposed surface of the flexural resonator 10 can optionally further comprise one or more external overlayers 30 (e.g., as an external coating or external layer), shown (for clarity) in the figure as partially covering the end of tine B of the tuning fork resonator. Preferably if an external overlayer 30 is provided, such external overlayer 30 can be configured to have an external surface 31 such that the exposed surface of the sensing element 10 consists essentially of the external surface 31 of the overlayer 30. In a particularly preferred embodiment, the overlayer 30 can be configured to operate as an additional electrode (e.g., as a conductive overlayer), for example, as a third electrode in the depicted embodiment of FIGS. 1A and 1B, such that the internal surface 32 of the overlayer 30 is in electronic association with the piezoelectric material. If the flexural resonator 10 has only a single first embedded electrode, then the external electrode comprising overlayer 30 can be a second electrode, with at least a portion of the second electrode having a first surface and a second surface, the first surface thereof being in electronic association with the piezoelectric material, the second surface thereof being configured such that the exposed surface of the sensing portion consists essentially of the second surface thereto. The conductive overlay can be of any suitable conducting material, including for example gold, silver, titanium, iron etc. In any of these embodiments, the one or more embedded electrodes (shown as 100, 200) and the external electrode (indicated in FIG. 1A as 300) can be configured so that upon activation, an electric field is generated between them within the piezoelectric material 20, and preferably so that the piezoelectric material 20 of the flexural resonator sensing element 10 resonates (e.g., tines A and B of the tuning fork resonator resonate).

In a particularly preferred embodiment, the one or more internal embedded electrodes 100, 200 and the external electrode 300 are configured such that upon activation, (i) the electric field generated between is substantially contained within the piezoelectric material, and (ii) the piezoelectric materials resonates. Advantageously, by providing an external electrode 300 that can be in electrical communication with a fluidic system ground, the flexural resonator 10 can be used in ionic liquid fluids without substantially affecting (e.g. compromising the quality of) the data due to conductivity of the fluid.

The external conductive overlayer (external electrode) can be operatively effective in two different approaches, each of which approaches can be employed in connection with each of the first, second, third and fourth general apparatus embodiments as described above, and further delineated hereinafter. Briefly, in one approach, the external electrode (conductive overlayer) can be effective without being electrically connected to the electronic circuitry used for providing a stimulating signal to the resonator and/or for receiving a response signal therefrom. In this approach, the conducting overlayer (external electrode) can act substantially as a faraday cage, effectively operating as a capacitive shield to substantially contain an electric field (generated by a pair of internal electrodes) within the mechanical resonator—that is to minimize the extent to which the electrical field within the piezoelectric resonator is coupled to the fluid under test during operation of the sensor. Preferably, during operation when configured according to this approach, the external electrode can be in contact substantially only with the fluid under test (and not with any structural feature that could provide an electrical communication back to the aforementioned circuitry). When configured according to this approach, the model circuit for the flexural resonator (e.g. such as a tuning fork resonator) can represented as in FIG. 8A, discussed in further detail below.

In an alternative approach, the external conductive overlayer (external electrode) can be grounded, and additionally or alternatively can be otherwise configured to form some portion of the electronic circuitry used for providing a stimulating signal to the resonator and/or for receiving a response signal therefrom. In such cases, appropriate adjustments and modifications can me made to derive a model circuit representative of such configuration.

Figure 1C:
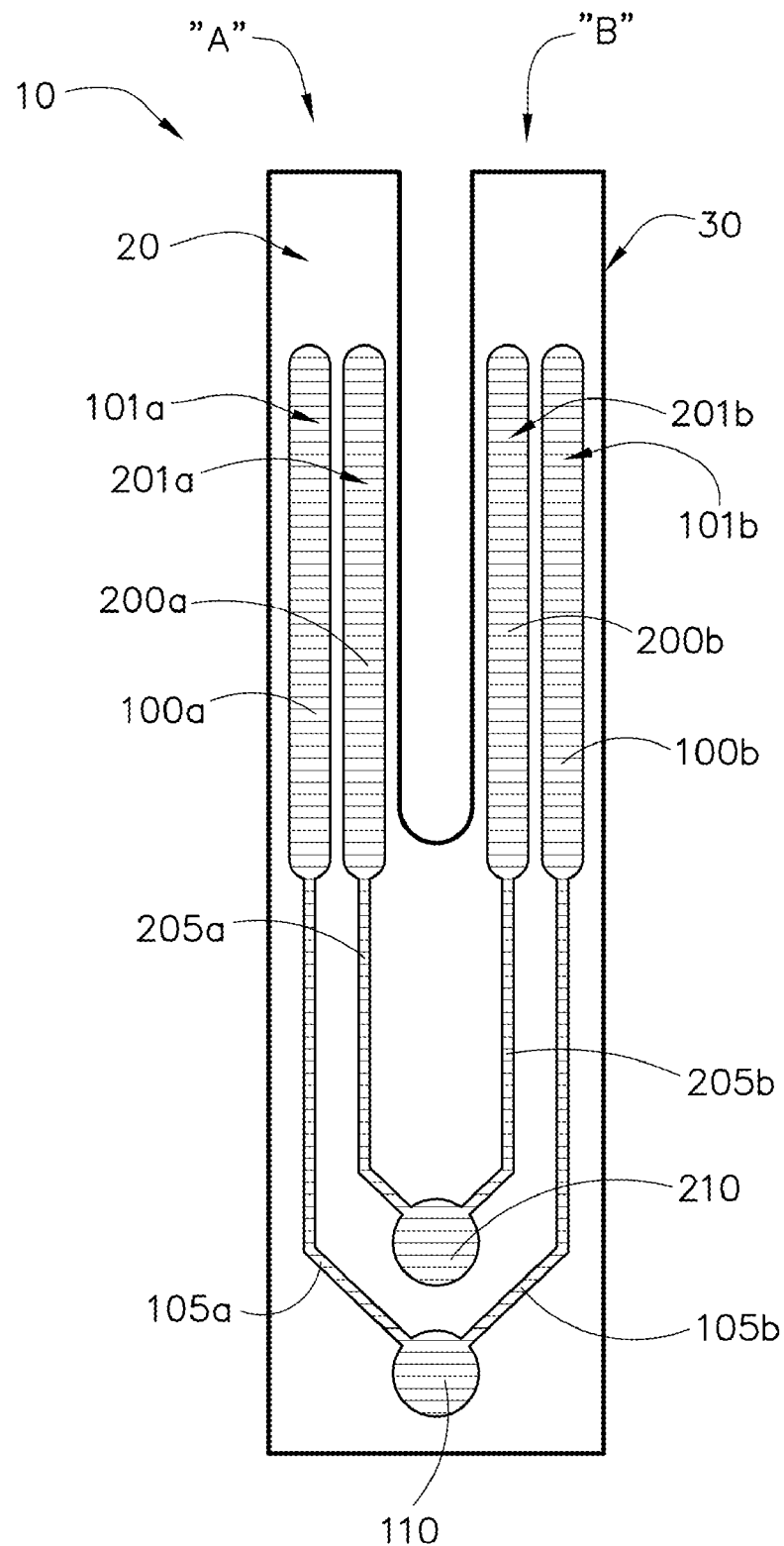

FIG. 1C shows a top cross sectional view of the flexural resonator 10 of FIG. 1A, taken in a plane that includes the embedded electrodes 100, 200. Like elements have been shown with the same reference numeral.

The following features as described hereinafter, are generally relevant to each of the aforedescribed general embodiments (first, second third embodiments) of the apparatus, and related embodiments of the systems and of the methods of the invention.

Generally, the piezoelectric material type is not narrowly critical. Preferred materials include, for example, quartz and lithium niobate, but any other material that exhibits a piezoelectric effect can be employed. Preferably, the material will be configured to displace a fluid upon activation (active sensing), and/or will, upon displacement by a fluid, generate an electric field that can be characterized by a generated signal.

Also, generally, the piezoelectric material 20 can be a unitary single material, or alternatively, can comprise two or more piezoelectric materials of the same type or of different types. Hence, in each of the embodiments of the invention, the flexural resonator can comprises a first piezoelectric material disposed over and electronically associated with the first surface of the electrode, and a second piezoelectric material disposed over and electronically associated with the second surface of the electrode. The first piezoelectric material and the second piezoelectric material can be the same type of piezoelectric material. Alternatively, the first piezoelectric material and the second piezoelectric material can be different types of piezoelectric material.

The first piezoelectric material and the second piezoelectric material can be physically contiguous with each other, or alternatively, the first and second piezoelectric materials can be physically discrete from each other. For example, the two piezoelectric materials can be separated from each other by one or more non-piezoelectric materials, such as an oxide layer. The distance of such separation (i.e., the thickness of such separating layer) is preferably minimized, if not substantially eliminated. Nonetheless, a relatively thin intermediate layer (e.g., even a non-piezoelectric layer) can be tolerated, for example, to obtain the benefit of preferred manufacturing approaches. For example, the intermediate, non-piezoelectric material can be an electrical insulator material or a material suitable for bonding. Generally, the thickness of the non-piezoelectric layer is substantially small so that it does not substantially adversely impact the extent of electronic association between the two separated piezoelectric materials, and/or adversely impact the extent of electronic association between an embedded electrode and one or more of the two separated piezoelectric materials. Hence, in the general embodiments described above, the first piezoelectric material can contact the first surfaces 101a, 101b, 201a, 201b of the electrodes. An intermediate material (e.g., an oxide layer) can be disposed between the second piezoelectric material and the second surfaces 102a, 102b, 202a, 202b of the electrodes. Preferably, the thickness of the second piezoelectric material is greater than the thickness of the intermediate material.

In general, a piezoelectric material is electronically associated with a surface of an electrode or with another piezoelectric material if either (i) an input signal applied to the electrode can generate an electric field at least partially within the piezoelectric material, manifested in that the piezoelectric material can displace a sensing surface of a flexural resonator comprising the piezoelectric material within a fluid, and additionally or alternatively, (ii) a displacement of a sensing surface of a flexural resonator comprising the piezoelectric material within a fluid can generate an electric field at least partially within the piezoelectric material, manifested in that the piezoelectric material can direct an output signal to the electrode. Hence in this context, and in the context of the previous discussion regarding an intermediate layer, it can be appreciated that in general, a piezoelectric material is disposed over a surface of an electrode if it is physically located directly or indirectly adjacent to that surface—either directly in contact therewith or indirectly situated in the near vicinity thereof—whereby a line taken perpendicular to the surface will intersect the piezoelectric material disposed thereover.

In general, the size of the mechanical resonator sensing elements such as flexural resonator sensing elements is not critical to the invention. In some applications, however, it should be appreciated that one advantage of the present invention is the ability to fabricate a very small sensor using the present resonators. For example, one preferred resonator has its largest dimension smaller than about 2 cm, and more preferably smaller than about 1 cm. One resonator has length and width dimensions of about 3 mm by about 12 mm, or alternatively of about 3 mm by about 8 mm, and possibly as small as about 1 mm by about 2.5 mm. Geometry of the resonator may be varied as desired also. For example, the aspect ratio of tines of the tuning forks, or geometrical factors of other resonators can be optimized in order to achieve better sensitivity to the properties of the gas phase, liquid phase or its particular components (e.g., a lubricant). For example, the aspect ratio of a tuning fork tine may range from about 30:1 to about 1:1. More specifically, it may range from about 15:1 to about 2:1.

Preparation of Flexural Resonator Having Embedded Electrode(s)

The manner in which the embedded electrode structure described above is prepared is not critical to the invention. Generally, any suitable technique can be applied. The apparatus of FIGS. 1A through 1C can be prepared, in one approach, using micromachining techniques known in the art.

Figure 2A:
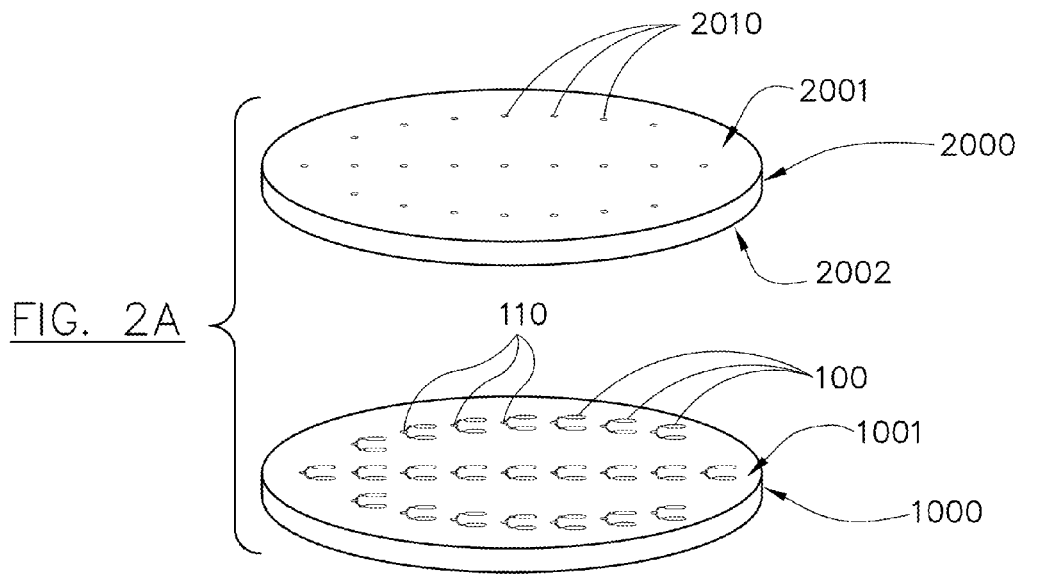
FIGS. 2A through 2J are schematic views of embodiments of the invention involving an array of tuning fork resonators having internal, embedded electrodes, as well as subassemblies thereof during a manufacturing protocol, including of a perspective view of first and second subassemblies (FIG. 2A), a top-plan view of a first subassembly (FIG. 2B), cross-sectional views of the first subassembly at intermediate stages of manufacturing (FIGS. 2C through 2E), a top-plan view of a second subassembly (FIG. 2F), a cross-sectional view of the second subassembly at an intermediate stage of manufacturing (FIG. 2G), a cross-sectional view of the completed assembly comprising the first and second subassemblies (FIG. 2H), a cross-sectional view showing an alternative embodiment (FIG. 2I), and a cross-sectional view taken orthogonally through both tines of the sensing portion of an embedded electrode tuning fork resonator resulting from (and depicting) the layered fabrication protocol (FIG. 2J).

Referring to FIG. 2A, for example, an array comprising a plurality of flexural resonators such as tuning fork resonators 10 (FIGS. 1A through 1C), each comprising one or more embedded electrodes 100, 200 can be formed from one or more substrates. Preferably, the substrates are a piezoelectric material, and preferably, are suitable for micromachining operations. For example, the substrates can be quartz or lithium niobate substrates. In one approach, a plurality of electrodes 100 can be patterned onto or into a first surface 1001 of a first piezoelectric material substrate 1000 using photolithographic patterning techniques and metal deposition techniques known in the art. The electrodes can be of any suitable conducting material, such as gold. Thereafter, a second piezoelectric material substrate 2000 can be bonded to the patterned substrate 1000, specifically by bonding a second surface 2002 of the second substrate 2000 to the first surface 1001 of the first substrate 1000. To facilitate bonding and/or manufacturing protocols, the first and/or second substrates 1000, 2000 may either or both further comprise an intermediate layer (not shown in FIG. 2A). The second wafer 2000 may further comprise, for example prior to bonding, a plurality of apertures 2010 each aligned for corresponding to a plurality of contact pads 110 associated with the plurality of patterned electrodes 100 on the first substrate 1000. The apertures 2010 may be prepared using any techniques suitable, such as drilling, including laser drilling. After bonding, these apertures 2010 may be used for providing electrical communication, preferably using conductive leads, between the contact pads of the electrode(s) and an electrical circuit, such as circuitry used for providing a stimulating signal to the resonator and/or for receiving a response signal therefrom. For example, the apertures 2010 can be operatively filled with a conductive material (e.g., gold) to create a conductive path between an exposed first surface 2001 of the second substrate 2000, and the contact pad 110 of the corresponding embedded electrode 100. Alternatively, conductive lead(s) can be inserted into the apertures, with exposed leads being electrically connected to the contact pads, for example, using a conductive epoxy or using wire bonding techniques as known in the art. As a further alternative, electrical connections to the contact pads of the electrodes can be provided using art-known contacts, such as pogo pins. If desired, the individual flexural resonators 10 can be formed, either before or after providing electrical connections. Preferably, the individual resonators can be formed before providing electrical connections. Preferably, the individual resonators can be formed by dicing the wafer stack according to methods known in the art, including for example use of dicing saws.

Figure 2C:
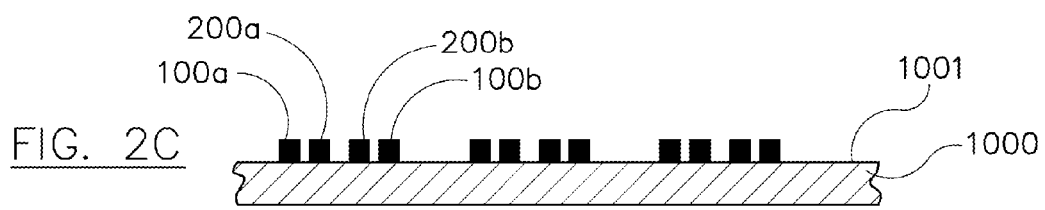
Figure 2D:
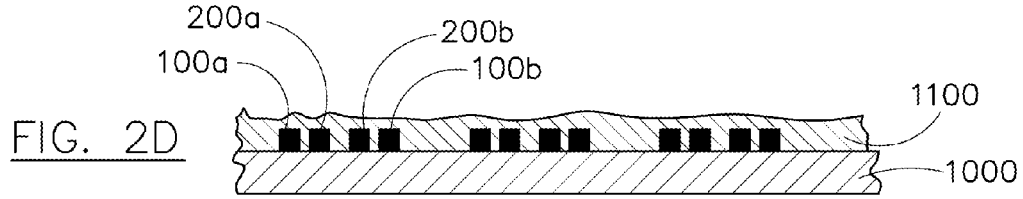
Figure 2E:
Figure 2H:
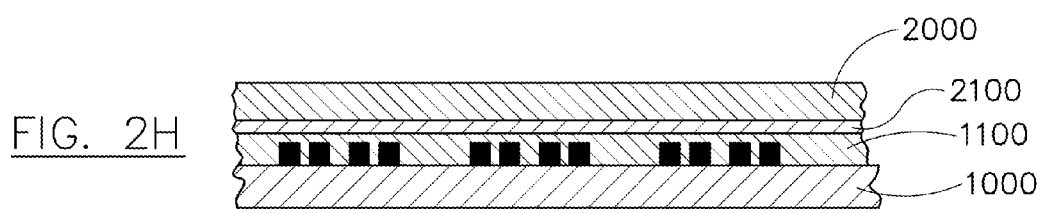
Figure 2B:
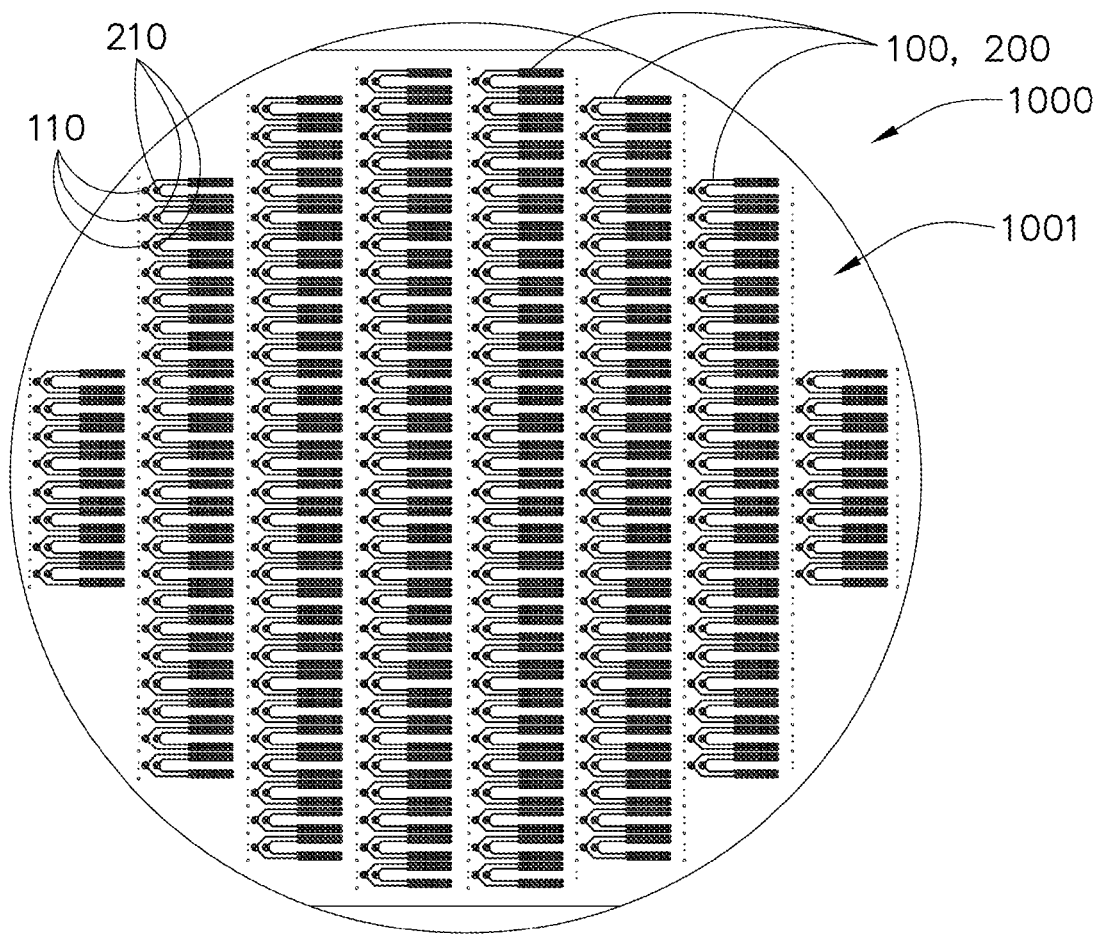
Figure 3:
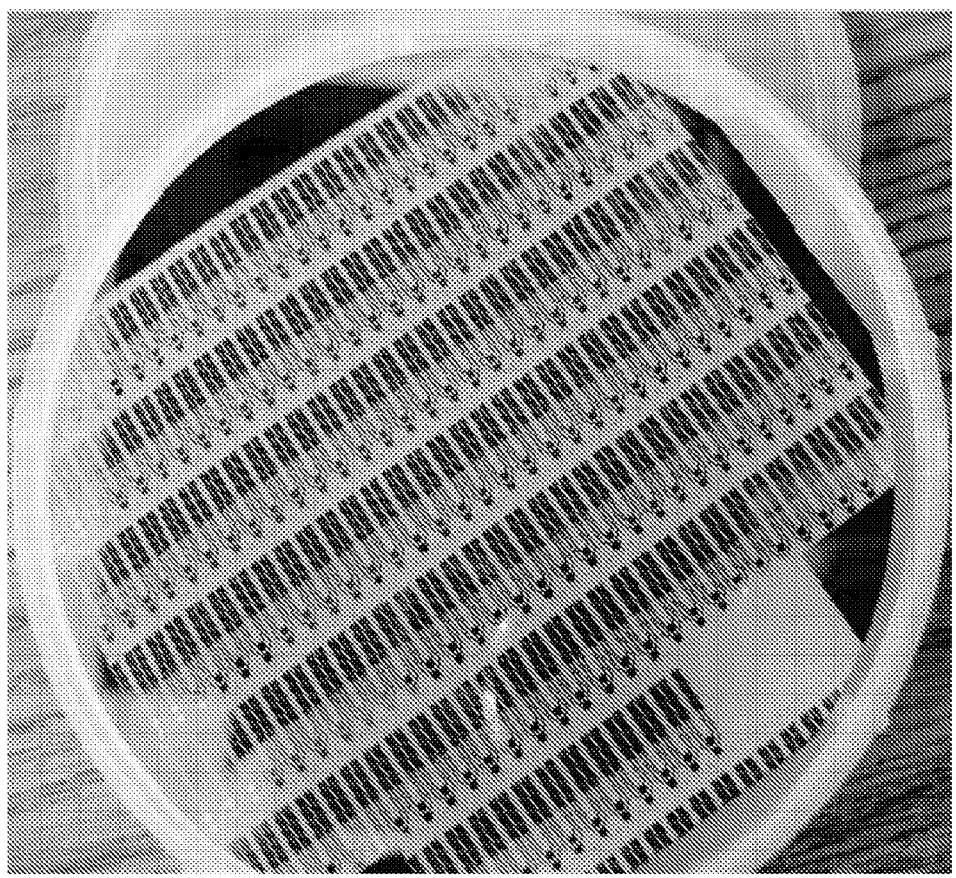
FIG. 3 is a photo of the first subassembly of the embodiment represented by FIGS. 2A through 2H at an intermediate stage of manufacturing.

Referring now to FIG. 2B (with further reference to FIGS. 1A through 1C) a first substrate 1000 having a first surface 1001 comprising a plurality of patterned electrode pairs 100, 200 can be prepared for use in preparing a plurality of flexural resonators as generally described above in connection with FIG. 2A. Briefly, referring to FIG. 2C, the electrode-patterned substrate 1000 can be formed by patterning a first substrate 1000 with positive or negative photoresist and then metal-depositing to form a plurality of electrodes 100*a*, 100*b*, 200*a*, 200*b* onto the first surface 1001 of the substrate 1000. An silica oxide overcoating 1100 can then be applied over the patterned plurality of electrodes 100*a*, 100*b*, 200*a*, 200*b*. (FIG. 2D) The oxide overcoating 1100 can be planarized and polished using known techniques to form a very thin oxide overlayer 1100 over the patterned plurality of electrodes 100*a*, 100*b*, 200*a*, 200*b*. (FIG. 2E, FIG. 2B). A photo is shown in FIG. 3.

Figure 2F:
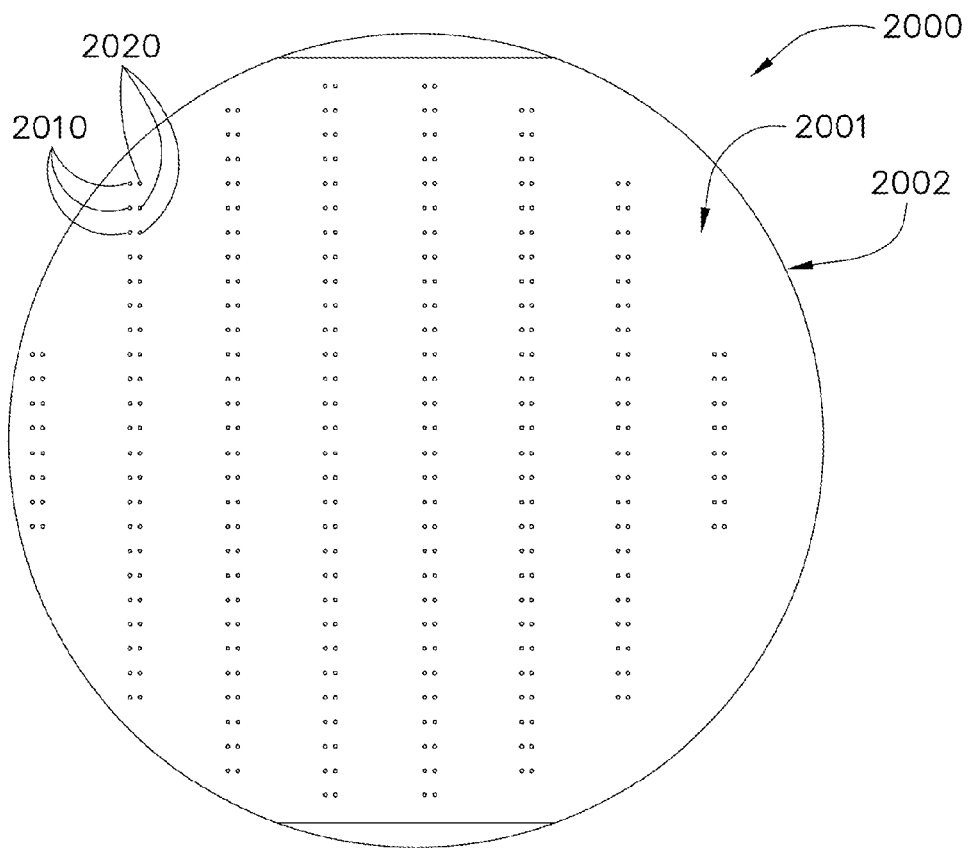
Figure 2G:
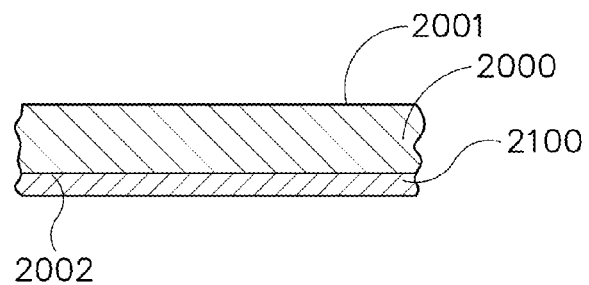

Referring now to FIG. 2F (with further reference to FIGS. 1A through 1C) a second substrate 2000 having a first surface 2001 and a second surface 2002 comprising a plurality of patterned apertures 2010, 2020 arranged to correspond to the plurality of contact pads 110, 201, respectively for the corresponding electrode pairs 100, 200 can be prepared for use in preparing a plurality of flexural resonators as generally described above in connection with FIG. 2A. Briefly, referring to FIG. 2G, the aperture—patterned substrate 2000 can be formed by first forming a second substrate 2000 having an oxide coating 2100 formed over its second surface 2002. The oxide coating 2010 can be planarized and polished (FIG. 2G). Apertures 2010, 2020 are then drilled, for example, by laser drilling in the required arrangement, to form the aperture-patterned second substrate 2000 (FIG. 2F).

Figure 4:
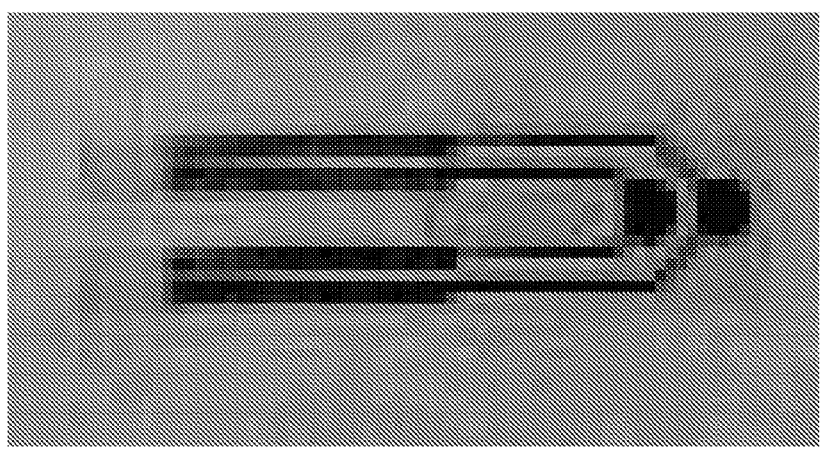
FIG. 4 is a photo of one tuning fork resonator diced from the completed assembly of the embodiment represented by FIGS. 2A through 2H.

Finally, the subassemblies comprising (i) the oxide-coated electrode-patterned first wafer 1000 (FIG. 2B) and (ii) the oxide-coated aperture-patterned second substrate (FIG. 2F) are then bonded (oxide surface to oxide surface) to form an array comprising a plurality of embedded electrodes. (FIG. 2H) Bonding can be effected by any appropriate means. Preferred bonding can be performed by commercially available techniques, including for example by companies such as Ziptronics, Inc. (Raleigh, N.C.). Dicing of the wafers can be done before or preferably after, bonding, by commercially available techniques, including for example by companies such as American Precision Dicing (CA). A photo of a patterned substrate 1000 diced into a tuning fork resonator is shown in FIG. 4.

Figure 2I:
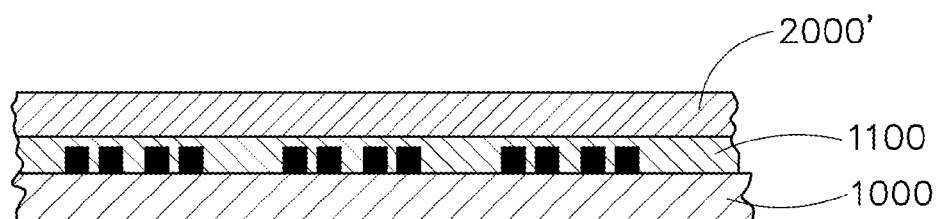

Referring now to FIG. 2I, in alternative embodiments the internal electrode(s) may have at least one surface (and in some embodiments, preferably only one surface) thereof in electronic association with a piezoelectric material 1000. The second surface of the internal electrode(s) can be in contact with a material other than a piezoelectric material that is a non-piezoelectric material (2000' as depicted in FIG. 2I). In such alternative embodiments, preferably, the mechanical resonator is a flexural resonator or a torsional resonator comprising a sensing portion having an exposed surface for contacting the fluid, and in particular, with the sensing portion of the mechanical resonator including at least one unrestrained end configured for sensing contact with the fluid (as described, for example generally above in connection with the fourth general embodiment of the of the invention). Preferably, the non-piezoelectric material is a substantially non-conducting material. The non-piezoelectric material can be, for example, an electrical insulator such as silicon oxide or silicon nitride. In these embodiments, as shown in FIG. 2I, the resonator comprises at a least one pair of electrodes configured for generating an electric field between them within the piezoelectric material. The mechanical resonator of these embodiments further comprises an external second electrode comprising a conductive overlayer, covering over at least the sensing portion of the mechanical resonator, including the at least one unrestrained end thereof. Preferably, the exposed surface of the sensing portion consists essentially of an exposed surface the conductive overlayer.

Figure 2J:
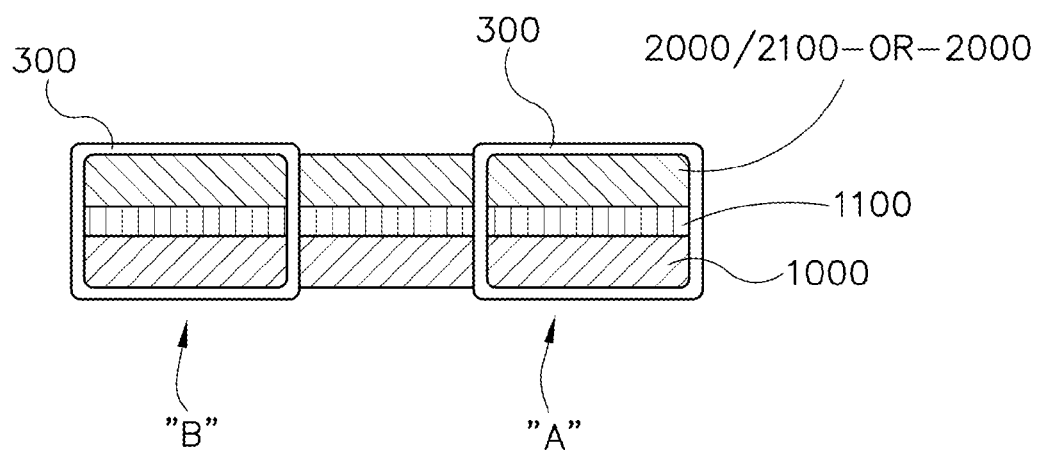

In any of the aforementioned embodiments, the resulting mechanical resonator can (after dicing the wafer to form individual resonators) comprise a layered structure, for example, as schematically represented in FIG. 2J for a tuning fork resonator. As shown therein, a resonator such as tuning fork resonator of the embodiment depicted in FIGS. 1A through 1C can comprise multiple layers, including at least an external conducting overlayer 300 (operative as an external electrode), the external conducting overlayer preferably being the exposed surface for the sensing portion of the resonator, a first layer 1000, the first layer being a piezoelectric material, an optional intermediate second layer 1100 (operative, for example, to facilitate bonding and/or to facilitate presentation of a planarized surface after deposition of internal electrodes, as described above), and a third layer 2000/2100 or 2000. The third layer can be, in preferred embodiments, a piezoelectric material (operative, for example, in connection with the piezoelectric material of the first layer). In alternative embodiments, the third layer can be a non-piezoelectric material, such as an insulator material (e.g., as described in connection with the fourth general embodiment hereof).

Monitoring of Fluidic Systems

In each of the aforementioned generally preferred approaches and/or embodiments, the fluidic system can be an open fluidic system or a closed fluidic system. An open fluidic system can comprise one or more fluids and having one or more fluidic surfaces that are exposed to an open uncontrolled atmosphere. For example, an open fluidic system can be an open container such as an open-top tank or an open well of a batch reactor or of a parallel batch reactor (e.g., microtiter plate). Alternatively, the fluidic system can be a closed fluidic system. A closed fluidic system can comprise one or more fluids that are generally bounded by a barrier so that the fluids are constrained. For example, a closed fluidic system can include a pipeline (e.g., for oil and/or gas transport) or a recirculating fluidic system, such as an oil system associated with an engine, or a refrigerant or coolant system with various residential, commercial and/or industrial applications. A closed fluidic system can be in fluid communication with an open fluidic system. The fluid communication between a closed fluidic system and an open fluidic system can be isolable, for example, using one or more valves. Such isolation valves can configured for uni-directional fluid flow, such as for example, a pressure relief valve or a check valve. In general, the fluidic system (whether open or closed) can be defined by manufactured (e.g., man-made) boundaries comprising one or more barriers. The one or more barriers defining manufactured boundaries barriers can generally be made from natural or non-natural materials. Also, in general, the fluidic system (whether open or closed) can be a flow system such as a continuous flow system or an intermittent-flow system, a batch system, or a semi-batch system (sometimes also referred to as a semi-continuous system). In many instances, fluidic systems that are flow systems are closed fluidic systems.

In general, the fluid in any of such fluidic systems can be a liquid or a gas. The particular type of liquid or gas is not narrowly critical. In particular, mechanical resonators such as flexural resonators can be used with a very large diversity of liquids or gasses. In particular, for example, mechanical resonators such as flexural resonators can be used in connection with liquids or gasses having a wide range of fluid properties, such as a wide range of viscosities, densities and/or dielectric constants (each such property being considered independently or collectively as to two or more thereof. The fluids of the invention can include relatively pure liquid or gaseous elements (e.g., liquid $N_2$, gaseous $O_2$, gaseous or liquid $H_2$) or relatively pure liquid or gaseous compounds (e.g., liquid $H_2O$, gaseous $CH_4$). The fluids of the inventions can also be single-phase or multi-phase mixtures of gases, liquids and/or solids, including for example: mixtures of gasses; mixtures of liquids (e.g., solutions); two-phase mixtures of a first liquid and a second liquid (e.g., liquid-liquid emulsion); two-phase mixtures of liquids and gasses (e.g., a liquid having gas sparging or bubbling, e.g., a liquid nebulized through a gaseous environment); two-phase mixtures of liquids and solids (e.g., colloidal solutions; dispersions; suspensions); two-phase mixtures of solids and gases (e.g., fluidized bed systems); and/or three-phase mixtures of gasses, liquids and solids. Particular examples of preferred fluids are described herein, including in discussion below regarding preferred applications of the methods and devices of the invention.

The operating conditions of the fluid in the fluidic system is not narrowly critical to the invention. Generally, the fluids within a particular fluidic system and/or fluids in different fluidic systems can have widely varying process conditions, such as temperature, pressure flowrate. Generally, the temperature can range from about or below the freezing point of the fluid to above the vaporization temperature, including for example to superheated temperatures and/or for supercritical fluids. Particular temperature ranges can be preferred for particular fluids. Generally, the pressure within a fluidic system can likewise cover a wide range, including for example ranging from about vacuum conditions to about 25,000 psig. In preferred applications, the pressure can be lower, ranging from vacuum conditions to about 15,000 psig, from vacuum conditions to about 10,000 psig, from vacuum conditions to about 5,000 psig, from vacuum conditions to about 1,000 psig, from vacuum conditions to about 500 psig, or from vacuum conditions to about 100 psig. In an alternative embodiment, the pressure range in each of the aforementioned ranges can have lower pressure limit of about 1 psig or about 10 psig or about 20 psig.

In the methods and systems and apparatus of the invention, the particular property being monitored is not narrowly critical. In general, the property of interest will depend on the fluid and the significance of the monitoring with respect to a particular fluidic system in a particular commercial application. The property being monitored for a particular fluidic system may also depend to some extent on the type of sensor. Significantly, some properties of fluids (both liquids and gasses) are of general importance across a wide range of commercial applications. For example, the viscosity of a fluid is of near universal interest for many fluidic systems. Likewise, the density of a fluid is also of great general interest for many fluidic systems. It is especially advantageous to be able to monitor both viscosity and density of a fluid—based on the same monitoring event (e.g., concurrently or simultaneously, using the same sensing element, on the same fluid sample). Significantly, flexural resonators such as tuning forks, unimorphs (e.g., disc benders), bimorphs, torsional resonators, etc. have been demonstrated by Matsiev et al. to have the capability of such concurrent or simultaneous monitoring of both viscosity and density. See Matsiev, "Application of Flexural Mechanical Resonators to Simultaneous Measurements of Liquid Density and Viscosity," IEEE International Ultrasonics Symposium, Oct. 17-20, 1999, Lake Tahoe, Nev. and EP 0943091 B1. See also U.S. Pat. Nos. 6,401,519; 6,393,895; 6,336,353; 6,182,499; and 6,494,079, each of which are incorporated by reference herein for all purposes. Dielectric constant is also a very significant property of interest for many commercial applications—particularly for applications involving ionic liquids. See Id. Other properties can also be of interest, alternatively to or in addition to the aforementioned properties. For example, temperature and/or pressure and/or flow rate are similarly of near-universal interest across a wide range of commercial applications. Parallel resistance can also be of interest.

In general, as noted above, the particular sensor of the methods and systems and apparatus of the present invention is not limited. Generally, the sensors useful in connection with this invention are adapted to monitor one or more properties of a fluid—that is, to generate data associated with one or more properties of the fluid. The data association with a property in this context means data (typically obtained or collected as a data stream over some time period such as a sensing period), including both raw data (directly sensed data) or processed data, can be directly informative of or related to (e.g., through correlation and/or calibration) an absolute value of a property and/or a relative value of a property (e.g., a change in a property value over time). In many applications, the raw data can be associated to a property of interest using one or more correlations and/or using one or more calibrations. Typically such correlations and/or calibrations can be effected electronically using signal processing circuitry, either with user interaction or without user interaction (e.g., automatically).

Particular sensors can be selected based on needed or desired property (or properties) of interest, and on required specifications as to sensitivity, universality, fluid-compatability, system-compatability, as well as on business considerations such as availability, expense, etc. Because of the substantial universal nature of viscosity and/or density and/or dielectric properties for many diverse fluidic systems, sensors that are suited for monitoring these properties are preferred. There are many sensors known in the art for measuring one or more of viscosity, density and/or dielectric. Accordingly, the selection of one or more of such sensor types is not critical to the invention.

Preferably, the sensor is a mechanical resonator sensor. The mechanical resonator can include, for example, flexural resonators, surface acoustic wave resonators, thickness shear mode resonators and the like. Various types of flexural resonators can be employed, including for example tuning forks, cantilevers, bimorphs, unimorphs, membrane resonators, disc benders, torsion resonators, or combinations thereof. Flexural resonator sensing elements comprising tuning fork resonators are particularly preferred. The tuning fork resonator can have two tines (e.g., binary-tined tuning fork) or more than two tines, such as three tines (e.g., a trident tuning fork) or four tines (e.g., a quaternary-tined tuning fork). In some applications, a tuning fork resonator may be configured (e.g., with respect to geometry and electrode configuration) for resonating within a single plane. For some applications, a tuning fork may be may be configured (e.g., with respect to geometry and electrode configuration) for resonating in two or more different planes relative to each other, such as in two planes perpendicular to each other.

Such flexural resonator sensors are well known in the art. See Matsiev, "Application of Flexural Mechanical Resonators to Simultaneous Measurements of Liquid Density and Viscosity," IEEE International Ultrasonics Symposium, Oct. 17-20, 1999, Lake Tahoe, Nev. and EP 0943091 B1. See also U.S. Pat. Nos. 6,401,519; 6,393,895; 6,336,353; 6,182,499; and 6,494,079, each of which are incorporated by reference herein for all purposes. More recent advances include those described in U.S. Pat. Nos. 7,043,969; 7,350,367; 7,210,332; and 6,873,916 and U.S. Pub. App. Nos. 2002/0178805 A1; and 2004/0250622 A1, each of which are incorporated herein by reference for all purposes, and each of which includes descriptions of some examples of flexural resonator sensors and use thereof in connection with the methods and apparatus and systems of the present invention. Further details regarding flexural resonator sensors and/or flexural resonator sensing element are described below, but are generally applicable to each approach and/or embodiment of the inventions disclosed herein.

Although much of the description is presented herein in the context of flexural resonator sensors, various aspects of the invention are not limited to such sensors.

Hence, other types of sensors (or sensor subassemblies) can also be used in place of mechanical resonators.

In addition, other sensors (or sensor subassemblies) can be used in combination with the mechanical resonator sensor or other types of sensors mentioned above. Particularly preferred sensors for use in combination with mechanical resonators, such as flexural resonators, include temperature sensors, pressure sensors, flow sensors, conductivity sensors, and thermal conductivity sensors, among others.

The methods and systems and apparatus of the invention can be used to monitor fluidic systems for various purposes. The inventions can be advantageously used, for example, to monitor fluids in any of the following field applications: materials or process research, materials or process development, materials or process quality assurance (QA), process monitoring/evaluation, process control, and service applications involving any of the foregoing.

Further details of preferred fluidic systems, fluids, properties, sensors and monitoring, including specific methodology approaches and apparatus features thereof are described herein (above and below), and each of the herein-described details are specifically considered in various combinations and permutations with the generally described aspects in this subsection of the specification.

Sensing with Flexural Resonator Sensor

The sensor can be advantageously applied to sense the fluid by collecting data, and typically a data stream that is fluid dependent, and that can be processed to identify and evaluate particular fluid property characteristics.

In any of the aforementioned and/or following-mentioned approaches and embodiments, the signal processing circuitry can comprise one or more circuit modules for processing data originating from the sensing element (generally, directly or indirectly). The signal processing circuitry can comprise each such circuit module alone (i.e., individually) or in various combinations and permutations. The data being processed can be raw data (previously unprocessed data) typically coming either directly from the sensing element or from a data storage media (i.e., data memory circuitry) that captured the data directly from the sensing element. Alternatively, the data being processed by one or more circuit modules of the signal processing circuit can be previously processed data (e.g., from another module thereof).

Generally, with reference to FIG. 5A and related figures, the sensor can comprise a sensing element 50, a signal processing circuit 20 and a data retrieval circuit 30.

The signal processing circuit 20 can comprise one or more circuits (or circuit modules) for activating a sensing element and/or for processing data originating with a sensing element, including generally for example: a signal activation circuit 22 (generally optional, e.g., for providing an electronic stimulus to the sensing element during active sensing, as discussed in more detail below); a signal conditioning circuit 24 for processing data originating from the sensing element (generally preferred, e.g., for altering an electronic characteristic of a data signal, typically resulting in a conditioned data or data stream); and/or a data derivation circuit 26 for processing data originating from the sensing element (generally preferred, e.g., for identifying, selecting or interpreting a particular electronic characteristic of a data signal, typically resulting in derived data or data stream that is more closely related to the property (or properties) of interest (e.g., has higher information content and/or greater information value) than a raw data stream and/or a conditioned data or data stream).

In particular, the signal processing circuit 20 can comprise one or more circuits (or circuit modules) as signal conditioning circuits 24, such as for example: signal input circuitry 24a (e.g., for receiving a response signal from the sensing element); amplifying circuitry 24b (e.g. including pre-amplifiers and amplifiers, for amplifying a signal); biasing circuitry 24c (e.g., for offsetting or otherwise changing a reference frame relating to the signal, including such as for reducing analog signal offsets in the response signal); converting circuitry 24d (e.g., analog-to-digital (A/D) converting circuitry for digitizing data or a data stream); microprocessor circuitry 24e (e.g., for microprocessing operations involving data originating from the sensing element and/or user-defined data); signal-processing memory 24f (e.g., typically being accessible to one or more signal processing circuits or circuit modules for providing data thereto, such as for example system-specific and/or sensing-element-specific identifying indicia, user-defined data for signal conditioning, etc.); and/or signal output circuitry 24g (e.g., for outputting a conditioned signal to another circuit module (e.g., to a data derivation circuit and/or to a data retrieval circuit).

Referring again to FIG. 5C, the signal processing circuit 20 can comprise one or more circuits (or circuit modules) as data derivation circuits 26, such as for example: signal input circuitry 26a (e.g., for receiving a response signal from the sensing element or from one or more data conditioning circuits 24); signal detection circuitry 26b (e.g., for identifying and/or detecting one or both of phase data and/or amplitude data and/or frequency data of the response signal); microprocessor circuitry 26c (e.g., for microprocessing operations involving data originating from the sensing element, typically involving a microprocessor configured for processing one or more software operations such as software algorithms or firmware algorithms (e.g., a data-fitting algorithm) for determining a parameter of the fluid that is associated with a property thereof, and/or typically for processing user-defined data (e.g., predefined data and/or substantially concurrently-defined data) in conjunction with the data originating from the sensing element, and/or typically involving user-initiated, user-controllable, and/or user-interactive processing protocols, typically for determining a parameter using a calibration with a fitting algorithm, for determining a parameter using a correlation algorithm, for determining a change in a detected signal characteristic (e.g., frequency, amplitude) or for determining a determined parameter); signal-processing memory 26d (e.g., typically including electronic data storage media, such as non-volatile memory (e.g., ROM, PROM, EE-PROM, FLASH memory, etc.), typically being pre-loaded with and/or being accessible for loading user-defined data (e.g., calibration data, correlation data, data defining approximated fluid properties, system-specific information, sensing-element specific information such as an identifying indicia, and/or typically being accessible to one or more signal processing circuits (or circuit modules) for use thereof; and/or signal output circuitry 26e (e.g., for outputting a conditioned signal to another circuit module (e.g., to a data derivation circuit and/or to a data retrieval circuit).

Likewise, in any of the aforementioned and/or following mentioned approaches and embodiments, referring again to FIGS. 5A and 5B, the data retrieval circuitry 30 can comprise one or more modules for retrieving data—whether raw data or processed data. Generally, the data retrieval circuit 30 can comprise one or more circuits (or circuit modules), including a data storage circuit 32, a data display circuitry 34 and/or a data transmission circuitry 36. The data retrieval circuit 30 can be in electrical communication with the sensing element directly, or alternatively, via a signal processing circuit 20 that processes (e.g., amplifies, biases, converts, etc.) raw data coming from the sensing element.

With further reference to FIG. 5C, the data storage circuit 32 can typically comprise: signal input circuitry 32a (e.g., for receiving raw data or a raw data stream from the sensing element, and/or for receiving conditioned data or a conditioned data stream from one or more data conditioning circuits 24, and/or for receiving derived data or a derived data stream from one or more data derivation circuits 26); a data storage media 32b (e.g., such as non-volatile memory (e.g., ROM, PROM, EE-PROM, FLASH memory etc.); and, signal output circuitry 32c (e.g., for outputting a stored data or stored data stream to another circuit module (e.g., to a data derivation circuit and/or to a data transmission circuit and/or to a data display circuit).

Data display circuit 34 as shown in FIG. 5C can configured to be effective for displaying data associated with one or more properties of a fluid, or for displaying a status of the fluid, where such status is based on data associated with a property of the fluid. Hence, data display circuit 34 can include a display device, and can typically comprise: signal input circuitry 34a (e.g., for receiving raw data or a raw data stream from the sensing element, and/or for receiving conditioned data or a conditioned data stream from one or more signal conditioning circuits 24, and/or for receiving derived data or a derived data stream from one or more data derivation circuits 26, and/or for receiving stored data or stored data stream from one or more data storage circuits 32); a data-display memory 34b (e.g., such as non-volatile memory (e.g., ROM, PROM, EE-PROM, FLASH memory, etc., or random access memory (RAM), in either case typically for temporarily storing a data or data stream to-be-displayed); a microprocessor circuit 34c (e.g., for processing/modifying data, such as stored, to-be-displayed data); a visual display circuit 34d (e.g., digital computer monitor or screen; e.g., a status light such as a LED status light, e.g., a printer, e.g., an analog meter, e.g., a digital meter, e.g., a printer, e.g., a data-logging display device, e.g., preferably in some embodiments a graphical user interface, etc.); and, signal output circuitry 34e (e.g., for outputting a stored data or stored data stream—such as to another circuit module (e.g., to a data derivation circuit and/or to a data transmission circuit and/or to a data display circuit).

Data transmission circuit 36 as shown in FIG. 5C can be configured to be effective for transmitting data originating from the sensing element. Specifically, for example, the data transmission circuit 36 can include: signal input circuitry 36a (e.g., for receiving raw data or a raw data stream from the sensing element, and/or for receiving conditioned data or a conditioned data stream from one or more data conditioning circuits 24, and/or for receiving derived data or a derived data stream from one or more data derivation circuits 26, and/or for receiving stored data or stored data stream from one or more data storage circuits 32); an optional microprocessor circuit 36b (e.g., for processing/modifying data, such as stored, to-be-transmitted data, and/or for controlling data transmission protocols); transmission protocol circuitry 36c (e.g., for effecting and coordinating communication protocols, such as for example a hard-wired interface circuit (e.g., TCP/IP, 4-20 mA, 0-5V, digital output, etc.), or a wireless communication circuit involving an electromagnetic radiation (e.g., such as radio frequency (RF) short range communication protocols (e.g., Bluetooth™, WiFi-IEEE Standard 80211 et seq., radio modem), land-based packet relay protocols, satellite-based packet relay protocols, cellular telephone, fiber optic, microwave, ultra-violet and/or infrared protocols), or a wireless communication circuit involving magnetic fields (e.g., magnetic induction circuits); and signal output circuitry 36d (e.g., for outputting a transmission of stored data or stored data stream—such as to another circuit module (e.g., to a data derivation circuit and/or to a data storage circuit and/or to a data display circuit).

Data transmission is particularly preferred using a data transmission circuit 36 in connection with a ported sensor subassembly that comprises a signal-processing memory and the data transmission circuit. Where the signal-processing memory comprises user-defined data, such data can be configured to be accessible to the data transmission circuit for communicating the user-defined data from the ported sensor subassembly to the fluidic system or to a remote data repository. In another preferred approach, the ported sensor subassembly can comprise a data transmission circuit for communicating data associated with one or more properties of the fluid from ported sensor subassembly to the fluidic system or to a remote data repository. In another method, the ported sensor subassembly can comprise a data storage media accessible for storing data associated with one or more properties of the fluid, and in combination therewith, a data transmission circuit for communicating stored data from the data storage media to the fluidic system or to a remote data repository, in either case preferably using a wireless communication protocol.

In any event, preferably, generated data is stored (e.g., in memory), displayed (e.g., in a graphical user interface or other display device) or (meaning additionally or alternatively) transmitted (e.g., using hard-wired or wireless communications protocols) using the data retrieval circuit of the interfaced sensor.

Although listed and represented in the figures in a particular (e.g., linear) order, there invention is not limited to use of such circuit modules in any particular order or configuration, and a person of ordinary skill in the art can determine a suitable circuit design for a particular fluidic system and a particular sensor, in view of the general and specific teaching provided herein.

Regardless of the particular configuration for the interfaced sensor, the fluid is sensed, actively or passively, using the interfaced sensor during a first sensing period to generate data associated with one or more properties of the fluid. In passive sensing mode of operation, the flexural resonator sensing element is displaced by the fluid to generate a signal (e.g., such signal being generated by piezoelectric material of sensing element, with appropriate electrodes), without application of an electronic input stimulus to the flexural resonator. In an active sensing mode of operation, an electronic stimulus (e.g., input signal having a voltage and/or frequency) is provided to the flexural resonator sensing element to initiate (via piezoelectric properties) a mechanical response in the sensing element such that at least a portion of the sensing surface of resonator displaces at least a portion of the fluid. The mechanical response is fluid dependent, and the extent of that dependence can be measured electronically, as is known in the art. With further reference to FIGS. 5B and 5C, a signal activation circuit 22 can comprise, for an active sensing mode of operation, a signal input circuitry 22a (e.g., for receiving a data or a data stream or instructions on active sensing signals) one or more user-defined or user-selectable signal generators, such as a frequency generator circuitry 22b, and/or such as a voltage spike generator circuitry 22c, and in each case, e.g., for providing an electronic stimulus to the sensing element, in an active sensing configuration; and signal output circuitry 22d.

In a preferred operation involving an active sensing mode, a stimulus signal (e.g., such as a variable frequency signal or a spike signal) can be intermittently or continuously generated and provided to the sensing element. A property-influenced signal, such as a frequency response, is returned from the sensing element. The return signal (e.g., frequency response) can be conditioned and components of the signal (e.g., frequency response) can be detected. The method can further include converting the frequency response to digital form, such that the digital form is representative of the frequency response received from the sensing element. Then, first calibration variables can be fetched from a memory. As used herein, the term "fetch" should be understood to include any method or technique used for obtaining data from a memory device. Depending on the particular type of memory, the addressing will be tailored to allow access of the particular stored data of interest. The first calibration variables can define physical characteristics of the sensor or sensing element. Second calibration variables can also be fetched from memory. The second calibration variables define characteristics of the sensor or sensing element in a known fluid. The digital form is then processed when the sensing element is in the fluid under-test, and the processing uses the fetched first and second calibration variables to implement a fitting algorithm to produce data that relates to the fluid properties or fluid characteristics of the fluid under-test.

In some embodiments involving an active sensing mode and using a mechanical resonator sensing element (such as a flexural resonator sensing element), it may be preferably to employ an active sensing mode of operation involving an input stimulus signal having a frequency of not more than about 1 MHz, and preferably not more than about 500 kHz, and preferably not more than about 200 kHz, and most preferably not more than about 100 kHz. In some embodiments, even lower frequencies can be employed in the operation of the mechanical resonator sensing element, including for example frequencies of not more than about 75 kHz. Specific operational ranges include frequencies ranging from about 1 kHz to about 1 MHz, preferably from about 1 kHz to about 500 kHz, preferably from about 1 kHz to about 200 kHz, preferably from about 1 kHz to about 100 kHz, preferably from about 1 kHz to about 75 kHz, more preferably from about 1 kHz to about 50 kHz, more preferably still from about 5 kHz to about 40 kHz, even more preferably from about 10 kHz to about 30 kHz and most preferably from about 20 kHz to about 35 kHz. In such embodiments, it may be preferably to provide an input stimulus signal that has a frequency that varies over time. In such embodiments, it may be preferably to provide two or more cycles of varying a frequency over time over a predetermined range of frequencies, and preferably over a frequency range that includes the resonant frequency for the flexural resonator sensing element. Such frequency sweeping offers operational advantages that are known in the art.

In a preferred operation involving a passive sensing mode, the sensing element, preferably a mechanical resonator such as a flexural resonator, interacts with the fluid to generate a property-influenced signal. The signal from the sensing element is intermittently or continuously observed and/or retrieved by the signal processing circuit. The signal can be conditioned and components of the signal (e.g., frequency response, voltage, etc.) can be detected. The method can further include converting the response to digital form, such that the digital form is representative of the signal received from the sensor. Then, as above in the active mode, first and/or second calibration variables can be fetched from a memory. The first calibration variables can define physical characteristics of the sensor or sensing element. Second calibration variables can also be fetched from memory. The second calibration variables can define characteristics of the sensor or sensing element in a known fluid. The digital form can then processed when the sensing element is in the fluid under-test, and the processing uses the fetched first and second calibration variables to implement a fitting algorithm to produce data that relates to the fluid properties or fluid characteristics of the fluid under-test.

In preferred embodiments, one or more circuit modules of the signal processing circuit and/or the data retrieval circuit can be implemented and realized as an application specific integrated circuit (ASIC). See, for example, above-referenced U.S. Ser. No. 10/394,543 entitled "Application Specific Integrated Circuitry For Controlling Analysis For a Fluid" filed on Mar. 21, 2003 by Kolosov et al., and PCT Application. No. PCT/US04/008555 entitled "Application Specific Integrated Circuitry For Controlling Analysis For a Fluid" filed on Mar. 19, 2004 by Kolosov et al. Particularly preferred circuit configurations are described below, but should be considered generally applicable to each approach and embodiment of the inventions described herein.

User-Defined Data (e.g., Calibration, Identifying Indicia)

Generally relevant to each of the methods, systems and apparatus of the inventions, user-defined data such as calibration data, correlation data, signal-conditioning data can be employed as part of a signal processing circuit (e.g., signal conditioning and/or data derivation circuitry). Likewise, additionally or alternatively, identifying indicia such as barcodes, electronic signatures (e.g., 64-bit serial numbers) can be used to identify one or more of: particular fluidic systems, particular locations within a fluidic system; particular fluid types; particular sensors; and/or particular sensing elements (including sensing element types (e.g., tuning fork flexural resonator), sensing element lot numbers for a set of co-manufactured sensing elements, and specific particular individual sensing elements). Such user-defined identifying indicia can be particularly useful in combination with user-defined calibration, correlation and/or signal conditioning data since such data can be specific to the fluidic system, the location, the fluid type; the sensor (type or individual sensor) and/or the particular sensing elements (including sensing element types (e.g., tuning fork flexural resonator), sensing element lot numbers for a set of co-manufactured sensing elements, and specific particular individual sensing elements). The user-defined data can be fluid-property (e.g., temperature dependent), and therefore, there can be interaction between one or more sensing elements (e.g., temperature sensing element) and a user-defined data (e.g., calibration data) for a particular fluid in a particular system using a particular resonator. The user-defined data can generally be pre-defined data or can be concurrently-defined data, and the defining can be done by a person and/or by a computer.

The level of specificity of any particular user-defined data to any particular fluidic system, fluid, sensor or sensor element will depend on the particular user-application, the property of interest, the sensor type, the required degree of accuracy, etc.

In a preferred methods, apparatus and systems, in which a flexural resonator sensing element is employed alone or in conjunction with one or more other systems, it is preferable to have accessible user-defined calibration data that includes at least (i) flexural resonator sensing element-specific (e.g., calibration) data, as well as (ii) application-specific (e.g., fluid type) data (e.g., calibration data). It is also preferable to have specific user-defined identifying indicia.

Sensors Having Flexural Resonator Sensing Elements and Operation Thereof

Figure 7A:
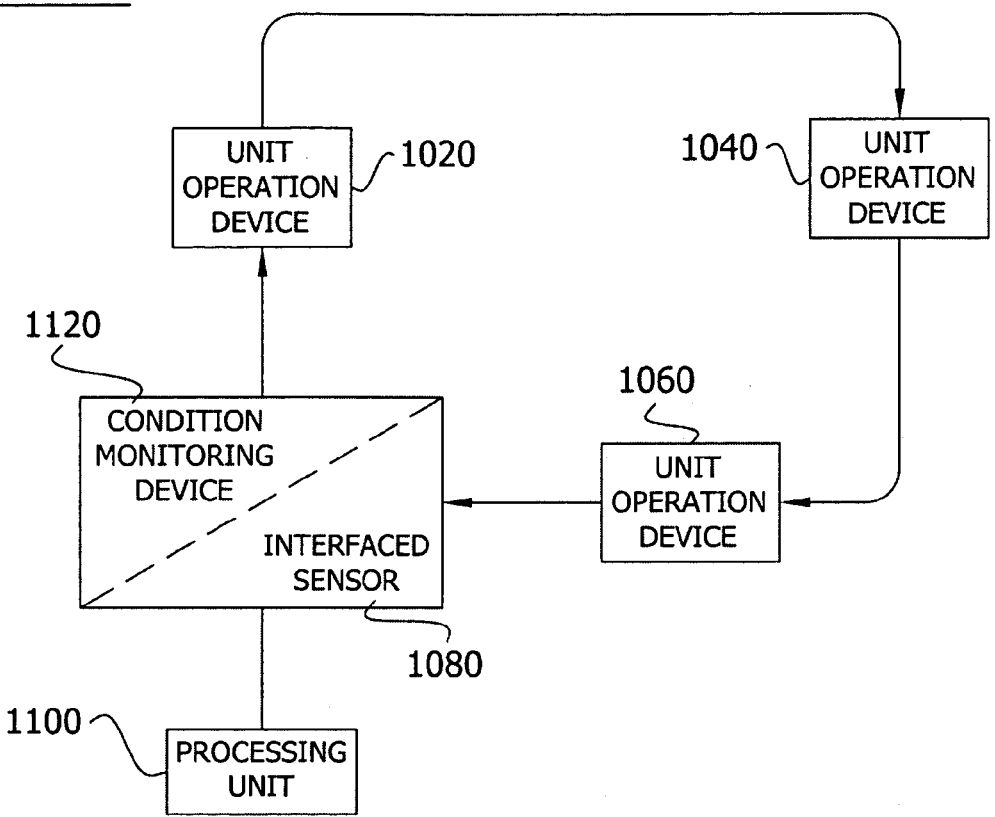

As seen in FIG. 7A, one embodiment involves the incorporation of a sensor according to the present invention into a fluidic system 1000, such as an environmental control system, that includes one or more unit operation devices 1020, 1040, 1060 such as a compressor, an expansion valve, a condenser and an evaporator through which a thermal change fluid can be cycled via one or more passages, such as in a conduit. Other components may also be employed as desired, such as one or more suitable pumps, a filter, a dryer, a suitable flow cell, or a combination of two or more thereof. Likewise, any of the above components may be omitted from a system of the present invention. Suitable valving and process monitoring instrumentation may also be employed in the fluidic system 1000.

One or more of the interfaced sensors 1080 according to the present invention is adapted for permanent or temporary placement within in one of the system components or between one of the system components. For example one or more sensors 1080 may be situated between various unit operation devices 1020, 1040, 1060. Likewise, one or more interfaced sensors may additionally or alternatively be incorporated in another component, such as a conduit, coil, filter, nozzle, dryer, pump, valve or other component, or positioned upstream or downstream therefrom. The sensor may be located in the flow path of the fluid (e.g., in a conduit), a headspace or both. In a particular embodiment, the sensor is included along with (and optionally integrated therewith) a condition monitoring device such as a temperature measurement device, a pressure measurement device, a mass flow meter, or combinations of two or more of such devices. Without limitation, an example of a combined pressure and temperature sensor is discussed in U.S. Pat. No. 5,586,445 (incorporated by reference).

Sensing in accordance with the present invention is particularly attractive for evaluating one or more of properties of the fluid, such as the level of a fluid (e.g., indicative of a system leak, a blockage in the system, or the like), the superheat condition of a fluid (e.g., the level of superheat), subcooling of a fluid, concentration of a desired component (e.g., refrigerant) in the fluid, or the presence or absence or concentration of an undesired component (e.g., contaminants) in the fluid. In particular, the sensor can be effectively employed to monitor (continuously or periodically) small changes in conditions of the fluid, such as viscosity, density, viscosity/density product, and in some embodiments, also dielectric constant, conductivity, and in all cases, various combinations of two or more thereof, which are indicative of a change of one or more of the above-noted properties, or of a change in state of the fluid or the presence of contaminants, and to output the results thereof.

Optionally, the interfaced sensor, the ported sensor subassembly, or the ported sensor can be in signaling communication with a processing unit 1100 (which may include a user interface) for controlling operation of the fluidic system. The processing unit 1110 may be microprocessor integrated into the ported sensor, the ported sensor subassembly or the interfaced sensor, for example, as part of the signal processing circuitry as described above. The processing unit 1100 optionally can optionally also be in signaling communication with a condition monitoring device 1120 (shown as part of an integrated assembly with the interfaced sensor 1080. Thus, data obtained from the interfaced sensor 1080 may be processed along with other data to assist in monitoring and establishing operating conditions of the fluidic system.

Thus, for example, in one aspect of the present embodiment, an interfaced sensor 1080 according to the present invention is employed to monitor at least one property of a fluid (e.g., the simultaneous monitoring of viscosity and density). Data generated from the sensor, along with other data (e.g., temperature, pressure, flow rate, or combinations thereof), for example, from the condition monitoring device 1120, can be sent to the processing unit 1100. From the data provided, the processing unit 1110, which typically will be programmed with a suitable algorithm, will process the data. In a process control embodiment, the processing unit can effect least one operation of the fluidic system selected from switching a subsystem of the fluidic system (e.g., a unit operation device 1020, 1040, 1060) or one or more components thereof between an "on" or "off" state, shutting or opening a valve in the fluidic system, changing a flow rate of the fluid, changing a pressure of the fluid, changing the operating speed or condition of one or more components of the fluidic system, or otherwise controlling operation of the fluidic system or a component thereof, providing a visual output signal, providing an audible output signal, or a combination thereof.

It will be appreciated that the above configuration of FIG. 7A permits the use of one or more modes of active sensing operations, such as excitation at one or more frequencies around resonance frequency of the resonator, or the time decay of oscillation after an electrical or mechanical impulse (e.g., a voltage spike). Passive operations can include, for example, observing passive oscillations due to ambient noise, vibrations, electromagnetic interference, etc.

The monitoring of fluid properties according to the invention may be performed under normal operating conditions of the machine into which the present sensor is placed. The present invention is particularly advantageous in that it operable over a broad range of temperatures. Thus, in one specific aspect, it is contemplated that the monitoring step occurs at a temperature below −40° C. or possibly the monitoring step occurs at a temperature above 400° C. Generally the monitoring will occur between these extremes.

It is also possible that during or following monitoring, the response of the sensor is compared against another value, such as a prior response of the resonator, a response of another resonator located elsewhere in the system, a known reference value for the fluid, or a combination of two or more such comparisons. The observed response may be stored in memory or otherwise recorded. It may also be possible to have data about a particular fluid stored in memory of a suitable processor, which can be retrieved in response to a triggering event, such as inputting by a technician or reading of a fluid type by an optical detector, such as a bar code scanner.

As the fluid property changes over time, analysis can be made and the response compared with those of the fresh fluid. The identification of a difference between responses could then be used as a trigger or other output signal for communicating with diagnostics hardware, which would provide an audible or visual signal to the operator. It is also possible that a signal is outputted to a remote telemetry device, such as one located external of the system. Thus, as with any of the embodiments herein a "wireless" communications system might be employed, pursuant to which a signal that is outputted may be a radiofrequency signal or another electromagnetic signal. Comparison against reference values from the original fluid is not the only approach for generating a communication to a user about the fluid condition. It may be possible, for example, to pre-program certain expected values into a device, which then compares the real-time values obtained to the expected values. Moreover, it is possible that no comparisons are made, but rather upon obtaining a certain threshold response, an output signal is generated for triggering a user notification, for triggering a system control unit to alter one or more functions of the system or a combination thereof. It is also contemplated that a sensor in a controlled fluid sample may be employed as an internal reference.

It is also possible that the response obtained from the monitoring is stored in a memory, with or without communicating the response to the user. In this manner, a service technician can later retrieve the data for analysis.

Figure 7B:
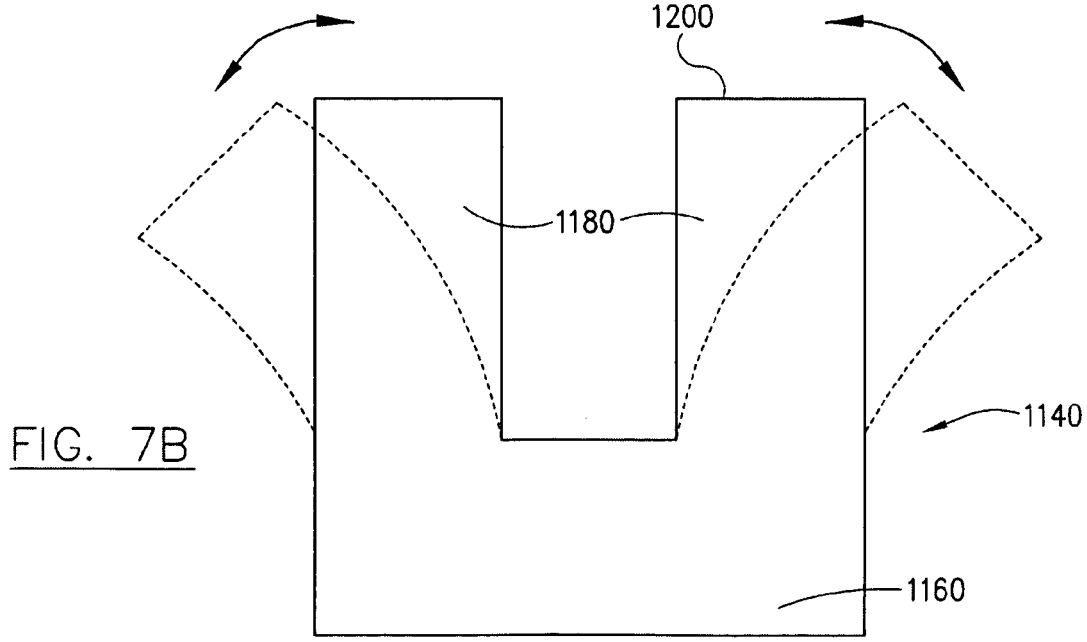

Turning now to FIG. 7B there is shown an illustration of one preferred resonator element 1140 in accordance with the present invention. The resonator element 1140 preferably includes a base 1160 that has at least two tines 1180 having tips 1200 that project from the base. The shape of the tines and their orientation relative to each other on the base may vary depending upon the particular needs of an application. For example, in one embodiment, the tines 1180 are generally parallel to each other. In another embodiment the tines diverge away from each other as the tips are approached. In yet another embodiment, the tines converge toward each other. The tines may be generally straight, curved, or a combination thereof. They may be of constant cross sectional thickness, of varying thickness progressing along the length of the tine, or a combination thereof.

Resonator sensing element(s) are suitably positioned in an element holder. Alternatively, the elements (with or without a holder) may be securably attached to a wall or barrier or other surface defining one of the fluidic systems or passages into which it is placed. In yet another embodiment, the element is suitably suspended within a passage such as by a wire, screen, or other suitable structure.

Element holders may partially or fully surround the sensing elements as desired. Suitable protective shields, baffles, sheath or the like may also be employed, as desired, for protection of the elements from sudden changes in fluid flow rate, pressure or velocity, electrical or mechanical bombardment or the like to help locate an element relative to a fluid or combinations thereof. It should be appreciated that resonator elements may be fabricated from suitable materials or in a suitable manner such that may be employed to be re-useable or disposable.

Examples of approaches to materials combinations, or the packaging of sensing elements that may be employed in accordance with the present invention are disclosed, without limitation in commonly-owned U.S. Provisional Application Ser. Nos. 60/456,767 and 60/456,517 (both filed Mar. 21, 2003) (and incorporated by reference). Thus, one particular approach contemplates affixing a sensing element having a exposed sensing surface to a platform, wherein a spaced relationship is created between the exposed sensing surface and the platform. A suitable protective layer may be applied to cover the platform and/or the sensing element while maintaining an exposed sensing surface. The latter exposed sensing surface may be prepared by the use of a consumable protective layer (e.g., a polymer, starch, wax, salt or other dissolvable crystal, low melting point metal, a photoresist, or another sacrificial material) that is used to block the exposed sensing surface prior to applying the protective layer.

A plurality of the same type or different types of resonators of resonators can be used in combination. For example, a low frequency resonator may be employed with a high frequency resonator. In this manner, it may be possible to obtain a wider range of responses for a given sample.

It is thus seen that a preferred resonator is configured for movement of a body through a fluid. Thus, for example, as seen in FIG. 7B, the resonator may have a base and one or a plurality of tines projecting from the base. It is preferred in one aspect that any tine has at least one free tip that is capable of displacement in a fluid relative to the base. FIG. 7C illustrates a cantilever 1220 having a base 1240 and a free tip 1260. Other possible structures, seen in FIGS. 7D and 7E contemplate having a disk 1280, a plate 1300 or the like that is adapted so that one portion of it is displaceable relative to one or more variable or fixed locations 1320 (1320'). As seen in FIG. 7F, in yet another embodiment a resonator 1340 is contemplated in which a shear surface 1360 of the resonator has one or more projections 1380 of a suitable configuration, in order that the resonator may be operated in shear while still functioning consistent with the flexural or torsional resonators of the present invention, by passing the projections through a fluid.

Figure 7G:
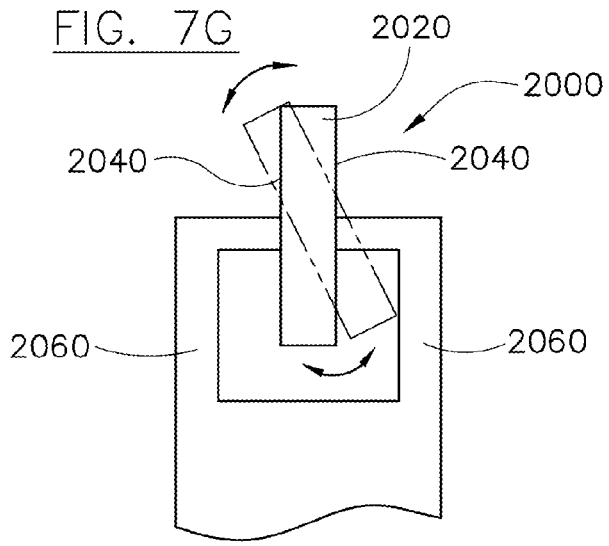
Figure 7H:
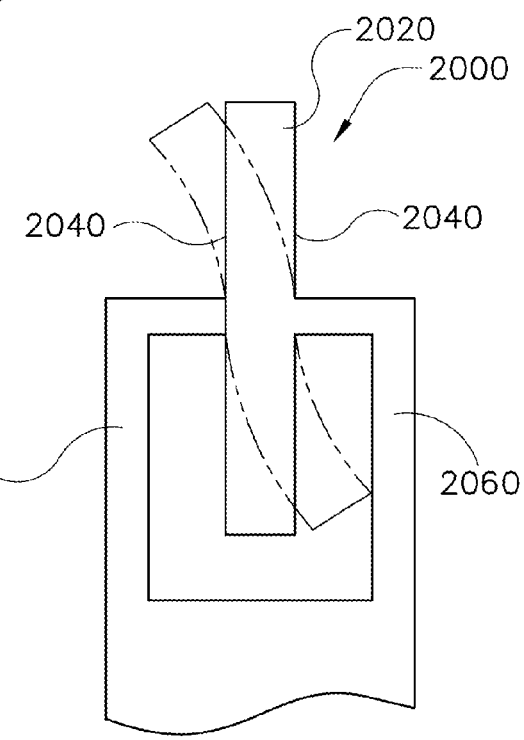
Figure 7I:
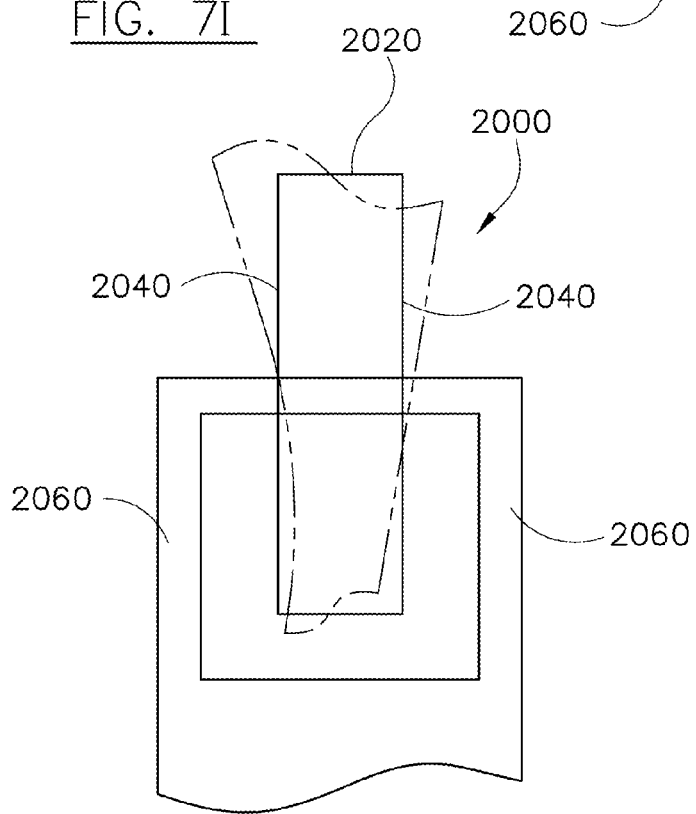

In still other embodiments, and referring to FIGS. 7G, 7H and 7I, it is contemplated that a resonator 2000 may include an elongated member 2020 supported on its sides 2040 by a pair of arms 2060. As shown respectively in FIGS. 7G through 7I, the elongated member may be configured to oscillate side-to-side, back and forth, in twisting motions or combinations thereof.

The flexural resonator, such as the embodiment of FIG. 7B, may be constructed as a monolithic device. Yet another structure of the present invention contemplates the employment of a laminate or other multi-layer body that employs dissimilar materials in each of at least a first layer and a second layer, or a laminate comprised of layers of piezoelectric material of different orientations or configurations. According to this approach, upon subjecting one or more of the layers to a stimulus such as temperature change, an electrical signal or other stimulus, one of the materials will respond different than the other and the differences in responses will, in turn, result in the flexure of the resonator. In yet another embodiment, it is contemplated that plural resonators can be assembled together with an electrode at least partially sandwiched therebetween. In this manner, it may be possible to further protect electrodes from harsh conditions, while still achieving the desired flexure. One specific example might include a two or more lithium niobate or quartz tuning forks joined together with a gold electrode therebetween. Other configurations (e.g., an H-shaped resonator) and material combinations may be employed as well, as disclosed in U.S. Provisional Application Ser. Nos. 60/456,767 and 60/456,517 (both filed Mar. 21, 2003), incorporated by reference.

As can be seen, the selection of the specific resonator material, structure, or other characteristic will likely vary depending upon the specific intended application. Nonetheless, it is preferred that for each application, the resonator is such that one or a combination of the following features (and in one highly preferred embodiment, a combination of all features) is present: a coating, if placed upon the resonator in a thickness greater than about 0.1 micron, preferably ranging from about 0.1 micron to about 500 microns will not substantially detract from resonance performance; the resonator is operable and is operated at a frequency of less than about 1 MHz, and more preferably less than about 100 kHz; the resonator is substantially resistant to contaminants proximate to the sensor surface; the resonator operates to displace at least a portion of its body through a fluid; or the resonator responses are capable of de-convolution for measuring one or more individual properties of density, viscosity, viscosity/density product, and in some embodiments also conductivity or dielectric constant.

The resonator may be uncoated or coated or otherwise surface treated over some or all of its exterior surface. A preferred coating is a metal (e.g., a conductive metal similar to what may be employed for electrodes for the sensor, such as silver, gold, copper, aluminum or the like), plastic, ceramic or composite thereof, in which the coating material is substantially resistant to degradation from the fluid to which it is to be exposed or to surface build-up, over a broad temperature range. For example, one preferred embodiment, contemplates the employment of a base resonator material and a performance-tuning material. Among the preferred characteristics of the resonators of the present invention is the base material is generally thermally stable. For example, in one preferred embodiment, the material exhibits a dielectric constant that is substantially constant over a temperature range of about 0° C. to about 100° C., more preferably about −20° C. to about 150° C., and still more preferably about −40° C. to about 200° C. For example, it is contemplated that a preferred material exhibits stability to a temperature of at least about 300° C., and more preferably at least about 450° C. In another aspect, the dielectric constant of the performance-tuning material preferably is greater than that of quartz alone, such as by a factor of 5 or more, more preferably by a factor of 10 or more and still more preferably by a factor of 20 or more.

Figure 8A:
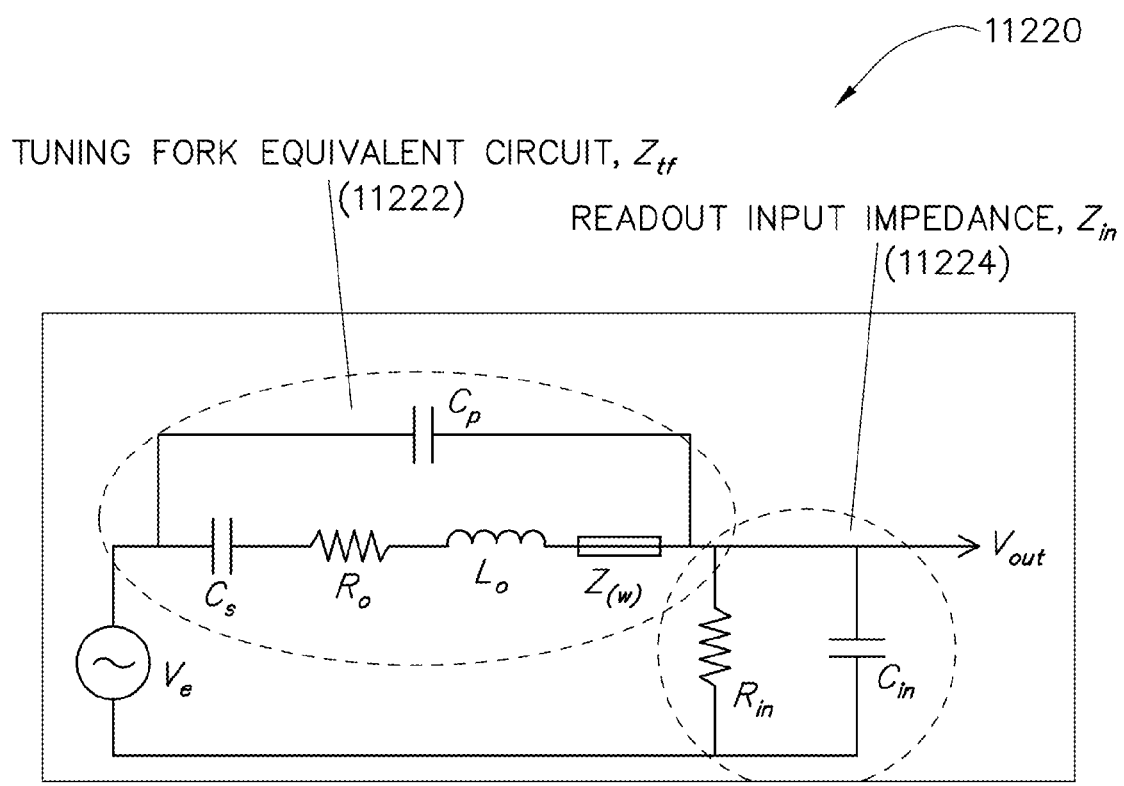
FIG. 8A is a schematic representation of an equivalent circuit for a sensor comprising a flexural resonator sensing element.

FIG. 8A illustrates a circuit diagram 11220 for a tuning fork equivalent circuit 11222 and a read-out input impedance circuit 11224. The frequency generator is coupled to the tuning fork equivalent circuit 11222 to a parallel connection of a capacitance Cp as well as a series connection of a capacitor Cs, a resistor Ro, an inductor Lo, and an equivalent impedance $Z(\omega)$. The read-out impedance circuit includes a parallel resistor Rin and a capacitor Cin. The output voltage is thus represented as Vout.

The following equations can define the equivalent circuit:

$$V_{out}(Co, Cp, Lo, Ro, Z(w), A, B, \rho, \eta, \omega, \epsilon) \quad (1)$$

$$V_{out}(\omega) = V_o(Z_{in}(\omega))/(Z_{in}(\omega)) + (Z_{tf}(\omega)) \quad (2)$$

$$Z_{in} = R_{in} * (1/i\omega C_{in})(R_{in} 1/i\omega C_{in})^{-1} \quad (3)$$

$$Z_{tf} = (1/i\omega Cp)(Ro+1)/i\omega Cs + i\omega Lo)(1/i\omega Cp + Ro + 1/i\omega Cs + i\omega Lo)^{-1} \quad (4)$$

$$Z(\omega) = Ai\omega\rho B * (\omega\rho\eta)^{1/2}(1+i) \quad (5)$$

$$\epsilon_{measured} = a + k * Cp_{(measured)} \quad (6)$$

$$\epsilon_{measured} = [\epsilon_{cal} - (\epsilon_{cal} - 1) * [CP_{cal}/(CP_{cal} - Cp_o)]] + [Cp_{(measured)} * [(\epsilon_{cal} - 1)/(CP_{cal} - Cp_{o(vacuum)})]] \quad (7)$$

$$a = [\epsilon_{cal} - (\epsilon cal - 1) * [Cp_{cal}/(CP_{cal} - Cp_o)]] \quad (8)$$

$$k = [[(\epsilon_{cal} - 1)/(CP_{cal} - CP_{o(vacuum)})] \quad (9)$$

$$Cp_{(measured)} \text{ IS A FUNCTION OF "k"} \quad (10)$$

In equation (2), the Vout of the equivalent circuit is defined. In equations (3) and (4), the impedance Zin and Ztf are derived. Equation (5) illustrates the resulting impedance over frequency $Z(\omega)$. As can be appreciated, the voltage Vout, graphed verses the frequency $Z(\omega)$, necessitates the determination of several variables.

The variables are defined in equation (1) of FIG. 8B. In operation, the tuning fork's frequency response near the resonance is used to determine the variables that will define the characteristics of the fluid-under-test. The algorithm that will be used to determine the target fluid under-test characteristic parameters will require knowledge of data obtained during calibration of a tuning fork. In addition to access to calibration data, the algorithm will also utilize a data fitting process to merge approximated variables of the target fluid under-test, to the actual variable characteristics (i.e., density, viscosity, dielectric constant) for the fluid under-test.

In the circuit, it is assumed that $C_S$, $R_O$, $L_O$ are equivalent characteristics of a preferred resonator in a vacuum, $\bar{C}p$ is the equivalent parallel capacitance in a particular fluid under-test, $\rho$ is the fluid density, $\eta$ is fluid viscosity, $\omega$ is oscillation frequency. Cp is a function of k, as shown in equations (6) through (10). The constant "k" is, in one embodiment, a function of the tuning fork's geometry, and in one embodiment, defines the slope of a curve plotting (Cpmeasured, Cpcal, and Cpvaccum) verses ($\epsilon$measured, $\epsilon$cal, and $\epsilon$vacuum), respectively. In a physical sense, the constant "k" is a function of the tuning fork's geometry, the geometry of the tuning fork's electrode geometry, the tuning fork's packaging (e.g., holder) geometry, the material properties of the tuning fork, or a combination of any of the above factors. The resulting-value of Cp will be used to determine the dielectric constant $\epsilon$ as shown by the equations.

Further, it can be appreciated that that viscosity and density can be de-convoluted based on the following equations:

$$Z(\omega) = Ai\omega\rho + B(\omega\rho\eta)^{1/2}(1+i)$$

$$Z(\omega) = i\omega\Delta Z(\omega)^{1/2}(1+i)$$

$$\Delta L = A\rho, \Delta Z = B(\rho\eta)^{1/2}$$

For some sensors, the value of $C_p$ measured is typically on the order of about 1 to 3 orders of magnitude greater than the value of $C_s$. Accordingly, in order to improve the ability to measure $Z(\omega)$, desirably trimming circuitry is employed as part of or in association with the signal conditioner, such as a trimming circuits. In order to more efficiently process the signal being received from the tuning fork, the signal is signal conditioned to eliminate or reduce the signal offset and thus, increase the dynamic range of the signal produced by the tuning fork. Thus, the data being analyzed can be more accurately processed.

FIGS. 9A through 9C and 10A through 10C represent one set of preferred approaches and embodiments for realizing a signal processing circuitry for a flexural resonator sensor. In particular, the described approaches and embodiments are considered in the context of an interfaced sensor applied with a fluidic system within an engine, and in particular, in combination with an engine control unit (ECU), which directs overall control of multiple aspects of engine operation. This should be understood as being an example demonstrating an application and manner of realizing the present inventions, and should not be limiting on the inventions described herein.

Figure 9A:
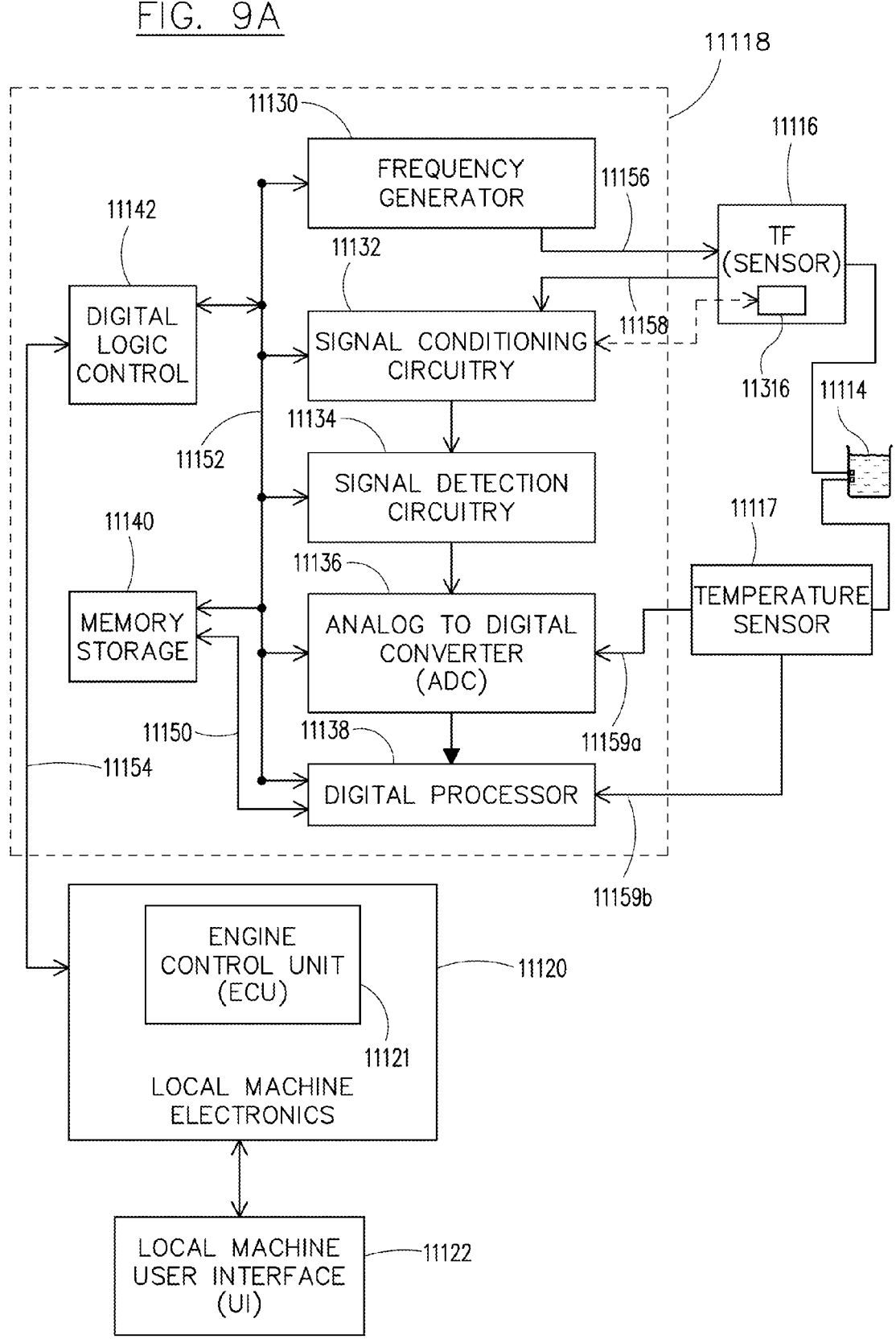

FIG. 9A illustrates a block diagram of the circuit formed, for example, in an application specific integrated circuit (ASIC) 11118 and its components, as an example of a signal processing circuit. The ASIC 11118 is designed to provide stimulus to the tuning fork 116 and receive and process data to provide information regarding the characteristics of a fluid under-test. In one embodiment, the ASIC will include a frequency generator 11130 that is configured to provide a frequency stimulus to the tuning fork 11116 by way of communication line 11156. The generated frequency is preferably a variable frequency input signal, such as a sinusoidal wave or square wave, that sweeps over a predetermined frequency range. The sweeping range will preferably include the resonance frequency range of the sensor. Preferably, the frequency is less than 100 kHz, and more preferably, is in the range of about 5 kHz and about 50 kHz, and most preferably, is in the range of about 20 kHz to about 35 kHz.

The tuning fork response over the frequency range is then monitored to determine the physical and electrical properties of the fluid under-test. The response from the tuning fork 11116 is provided to a signal conditioning circuitry block 11132, by way of a communication line 11158. In one preferred embodiment, the tuning fork 11116 will also include a capacitor 11316, which will be described in greater detail below. The capacitor 11316 is also coupled to the signal conditioning circuitry 11132. The signal conditioning circuitry 11132 is provided to receive the analog form of the signal from the tuning fork 11116 and condition it so that more efficient signal processing may be performed before further processing.

The signal conditioning circuitry 11132 will receive the analog output from the tuning fork 11116, and is designed to substantially eliminate or reduce signal offsets, thus increasing the dynamic range of the signal that is to be further processed. In this manner, further processing can concentrate on the signal itself as opposed to data associated with the signal offset.

Signal detection circuitry (SDC) 11134 is also provided, and it is coupled to the signal conditioning circuitry 11132. Signal detection circuitry 11134 will include, in one embodiment, a root mean squared (RMS) to DC converter, that is designed to generate a DC output (i.e., amplitude only) equal to the RMS value of any input received from the signal conditioning circuitry 11132. The functional operation of a RMS-to-DC converter is well known to those skilled in the art. In another embodiment, the signal detection circuitry 11134 may be provided in the form of a synchronous detector. As is well known, synchronous detectors are designed to identify a signal's phase and amplitude when preprocessing of an analog signal is desired in order to convert the analog signal into digital form. Once the signal detection circuitry block 11134 processes the signal received from the signal conditioning circuitry 11132, the signal detection circuitry 11134 will pass the data to an analog-to-digital converter (ADC) 11136. The analog-to-digital converter 11136 will preferably operate at a sampling rate of up to 10 kHz while using a 10-bit resolution. The analog-to-digital converter (ADC) can, of course, take on any sampling rate and provide any bit resolution desired so long as the data received from the signal detection circuitry is processed into digital form.

The ADC 11136 will also receive information from the temperature sensor 11117 to make adjustments to the conversion from the analog form to the digital form in view of the actual temperature in the fluid under-test 11114. In an alternative embodiment, the temperature sensor 11117 can be omitted, however, the temperature sensor 11117 will assist in providing data that will expedite the processing by the ASIC 11118.

The digital signal provided by the analog-to-digital converter 11136 is then forwarded to a digital processor 11138. The digital processor 11138 is coupled to memory storage 11140 by way of a data bus 1150 and a logic bus 11152. Logic bus 11152 is also shown connected to each of the frequency generator 11130, the signal conditioning circuitry 11132, the signal detection circuitry 11134, and the analog-to-digital converter 11136. A digital logic control 11142 is directly coupled to the logic bus 11152. The digital logic control 11142 will thus communicate with each of the blocks of the ASIC 11118 to synchronize when operation should take place by each one of the blocks. Returning to the digital processor 11138, the digital processor 11138 will receive the sensed data from the tuning fork 11116 in digital form, and then apply an algorithm to identify characteristics of the fluid under-test 11114.

The algorithm is designed to quickly identify variables that are unknown in the fluid under-test. The unknown variables may include, for example, density, viscosity, the dielectric constant, and other variables (if needed, and depending on the fluid). Further, depending on the fluid under-test 11114 being examined, the memory storage 11140 will have a database of known variables for specific calibrated tuning forks. In one embodiment, the memory storage 11140 may also hold variables for approximation of variables associated with particular fluids. In another embodiment, the memory storage 11140 will store serial numbers (or some type of identifier) to allow particular sets of data to be associated with particular tuning forks. In such a serial number configuration, the storage memory can hold unique data sets for a multitude of unique tuning forks. When a tuning fork is sold, for example, the purchaser need only input its assigned serial number into an interface, and the data set associated for that tuning fork will be used during operation. From time to time, it may be necessary to upload additional data sets to the storage memory 11140, as new tuning forks (with unique serial numbers) are manufactured.

The process for using variable data from prior calibrations and from fluids that may closely resemble the fluid under-test, will be described in greater detail below. In general, however, the digital processor 11138 may quickly access the data from the memory storage 11140, and digitally process an algorithm that will generate and output variables that define the fluid under-test 11114.

The digital processor will then communicate through the digital logic control 11142 and communication line 11154, the identified variables that characterize the fluid under-test 11114 to the local machine electronics 11120 (or some recipient computer, either locally or over a network). In one embodiment, the local machine electronics 11120 will include an engine control unit (ECU) 11121, that directly receives the data from the digital logic control 11142 through signal 11154. The engine control unit 11121 will then receive that data and, in accordance with its programmed routines, provide feedback to the local machine user interface 11122.

For example, the engine control unit 11121, may set a different threshold for when the fluid under-test 11114 (i.e., engine oil), has degraded. For example, different car manufacturers, and therefore, different engine control units for each car will define a particular viscosity, density and in some embodiments, dielectric constant (or one or a combination thereof) that may be indicative of a need to change the oil. However, this programmable threshold level setting will differ among cars. Thus, the engine control unit 11121 will provide the local machine user interface 11122 the appropriate signals depending on the programming of the particular automobile or engine in which the engine control unit 11121 is resident.

The ASIC 11118 has been shown to include a number of component blocks, however, it should be understood that not all components need be included in the ASIC as will be discussed below. In this example, the digital processor 11138 may be physically outside of the ASIC 11118, and represented in terms of a general processor. If the digital processor 11138 is located outside of the ASIC 11118, the digital logic control 142 will take the form of glue logic that will be able to communicate between the digital processor 11138 that is located outside of the ASIC 11118, and the remaining components within the ASIC 11118. In the automobile example, if the processor 11138 is outside of the ASIC, the processor will still be in communication with the engine control unit 11121.

Figure 9B:
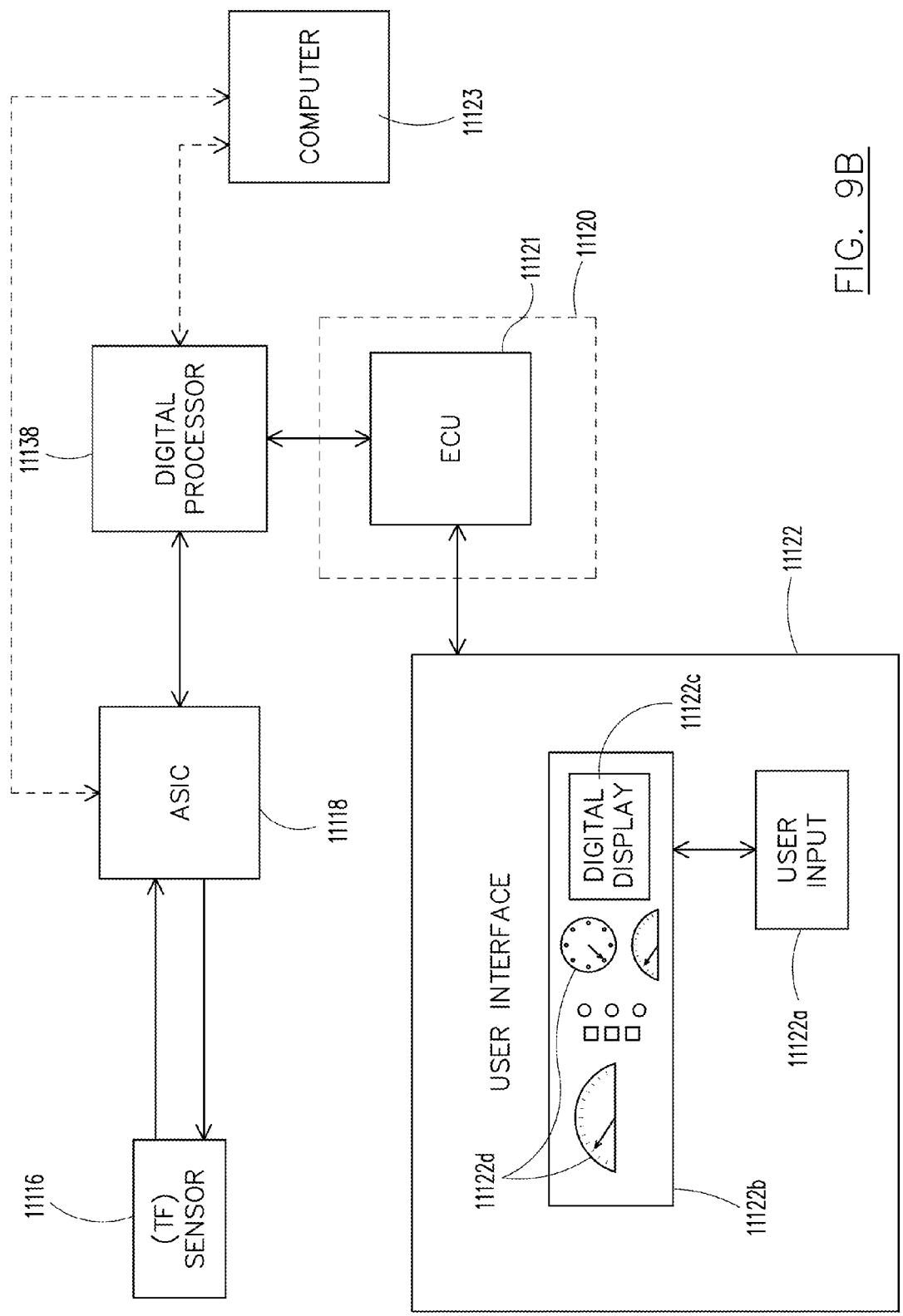
Figure 10A:
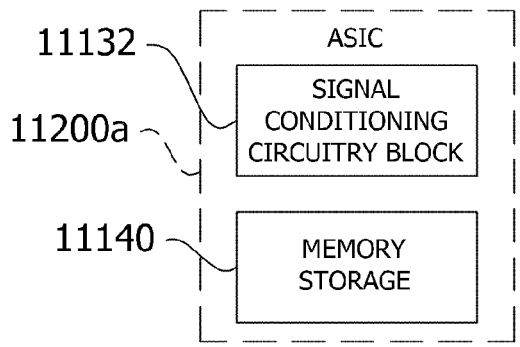
FIGS. 10A through 10D are schematic representations of alternative approaches for realizing circuitry in an ASIC.
Figure 10B:
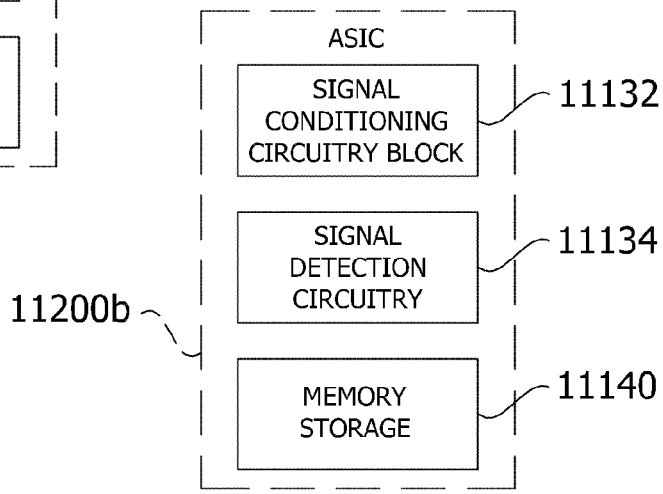
Figure 10C:
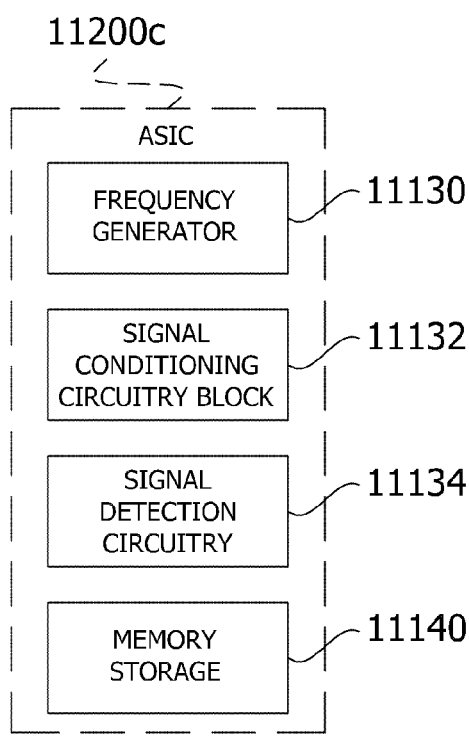
Figure 10D:
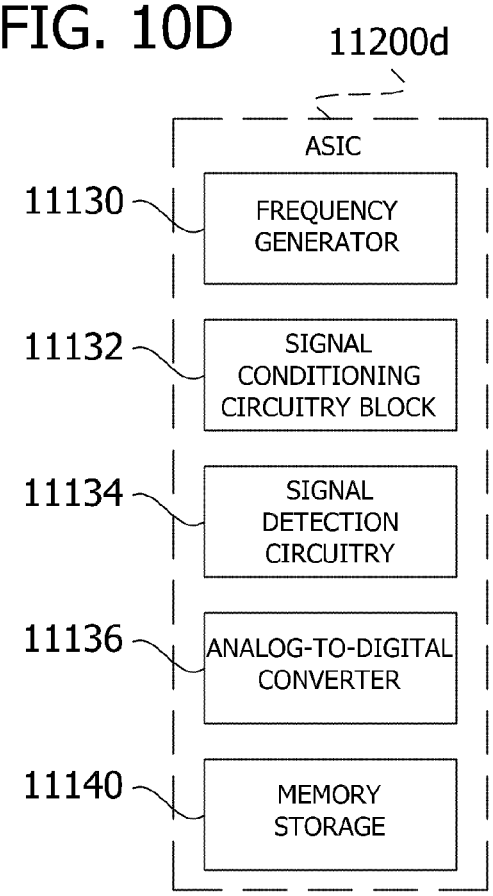

FIG. 9B illustrates an example when the digital processor 11138 is outside of the ASIC 11118. In such an embodiment, the digital processor 11138 may be integrated into a printed circuit board that is alongside of the ASIC 11118, or on a separate printed circuit board. In either case, the ASIC 11118 will be in communication with the tuning fork 11116 to provide stimulus and to process the received analog signals from the tuning fork 11116. The ASIC will therefore convert the analog signals coming from the tuning fork 11116 and convert them to a digital form before being passed to the digital processor 11138.

If the ASIC 11118 is provided on an automobile, and the digital processor 138 is outside of the ASIC 11118, the digital processor 11138 will still be able to communicate with the engine control unit 11121 of the local machine electronics 11120. The engine control unit 11121 will therefore communicate with the local machine user interface 11122. In this example, the user interface may include a user display 11122*b*. The user display 11122*b* may include analog and digital indicators 11122*d*. The analog and digital indicators 11122*d* may indicate the qualities of the fluid under-test (e.g., engine oil), and can be displayed in terms of a gauge reading to indicate to the user when the fluid under-test has degraded or needs to be changed.

In another embodiment, the user display 11122*b* may include a digital display 11122*c* (e.g., monitor) that may provide a digital output or display of the condition of the engine oil to the user through an appropriate graphical user interface (GUI). The user interface 11122 may also include a user input 11122*a*. The user input 11112*a* may be a electronic interface that would allow a service technician, for example, to provide updated calibration information for a tuning fork that is inserted in a particular vehicle, or provide adjusted approximations for new engine oils that may just have come onto the market.

By way of the user input 11122*a*, a service technician will be able to input new data to the ASIC 11118 through the engine control unit 11121. As mentioned above, the ASIC 11118 will include a memory storage 11140 for storing calibration data, and in some embodiments, storing approximated characteristics for fluids that may undergo sensing by tuning fork 11116.

FIG. 9C illustrates another detailed block diagram of the ASIC 11118, in accordance with one embodiment of the present invention. In this example, the ASIC 11118 shows a number of blocks that may be integrated into or kept out of, the ASIC 11118. Blocks that may be kept outside of the ASIC include blocks 11175. As a high level diagram, the tuning fork 11116 is connected to an analog I/O 11160. The analog I/O is representative of blocks 11132, 11134, and 11136, in FIG. 9A above. The analog I/O block 11160 therefore performs signal conditioning and conversion of the data received from the tuning fork 11116.

Frequency generator 11130, as discussed above, will provide the variable frequency input signal to the tuning fork 11116 through the analog I/O 160. Glue logic 11162 is provided to integrate together the various circuit blocks that will reside on the ASIC 11118. As is well known, glue logic will include signaling lines, interfacing signals, timing signals, and any other circuitry that is needed to provide inputs and outputs to and from the chip that defines the ASIC 11118. All such glue logic is standard and is well known in the art. The ASIC 11118 further includes user defined data (ROM) 11140'. As mentioned above, the user-defined data 11140' may include calibration data, as well as approximated variable data for particular fluids that may become fluids under-test. The user defined data to be stored in this memory can come from any source. For example, the data may be obtained from a fluid manufacturer, a tuning fork manufacturer, a contractor party, etc. Still further, the data may be obtained in the form of a data stream, a database or over a network.

For example, FIGS. 9D and 9E provide exemplary data that may be stored within the user-defined data 11140'. As shown in FIG. 9D, a tuning fork 1.1 (designated as such to emphasize varieties in tuning forks) may provide calibration variables, as well as approximated fluid characteristics for a particular type of fluid. In the example of FIG. 9D, the selected oil type 3 has approximated fluid characteristics for density, viscosity, and dielectric constant for a particular temperature, which is depicted in this figure to be 25° C. As used herein, the term "approximated fluid characteristics" represent starting point values of fluid characteristics before the fitting algorithm is started. Thus, the starting point values are initial values defined from experience, previous tests, or educated guesses. Consequently, the starting point values, in one embodiment, approximate the actual fluid characteristic values of the fluid under-test. In this manner, convergence to the actual fluid characteristics can be expedited.

In still another embodiment, it may be possible to start with the approximated fluid characteristics at some set of fixed values (which can be zero, for example). From each fixed value, the fitting algorithm can move the value until the actual fluid characteristic value is ascertained.

Continuing with the example, the approximated fluid characteristics for the same oil type 3 may have different approximated fluid characteristics due to the rise in temperature to 40° C., in FIG. 9E. The calibration variables will also be updated to reflect the values for a particular temperature for the tuning fork 1.1. As new oil types become available to the market, it may be necessary to update the approximated fluid characteristics for the different temperature ranges so that the user-defined data can be updated in the ASIC 11118.

Referring back to FIG. 9C, a digital I/O 11140' is provided to interface with a computer 11123, and a test I/O interface 11164 is provided to enable testing of the ASIC 11118 during design simulation, during test bench testing, during pre-market release, and during field operation. The ASIC 11118 will also include a timer 11172 to provide coherent operation of the logic blocks contained in ASIC 11118. As mentioned above, the ROM block 11166, the RAM block 11168, the CPU core 11170, and the clock 11174, can optionally be included in the ASIC 11118 or removed and integrated outside of the ASIC 11118. The ROM 11166 will include programming instructions for circuit interfaces and functionality of the ASIC 11118, the RAM 11168 will provide the CPU core 11170 with memory space to read and write data being processed by the CPU core 11170, and the clock 11174 will provide the ASIC with proper signal alignment for the various signals being processed by the blocks of the ASIC 11118.

FIGS. 10A through 10D depict alternative configurations for various circuit modules 11200*a*, 11200*b*, 11200*c*, 11200*d* of the ASIC 11118.

Downstream Data Processing

The methods and systems and apparatus of the invention can be used to monitor fluidic systems for various purposes. The inventions can be advantageously used, for example, to monitor fluids in any of the following field applications:

transportation (air, sea, land, space);
working vehicles (construction, agriculture, mining, subsea rov, trucking);
military vehicles (hmvee, tanks, trucks, etc.);
heavy machinery (industrial, manufacturing);
industrial wastewater;
drinking water;
oil and gas exploration and production (drilling, wellbore and production logging, laboratory oil analysis, separation);
fuel and hydrocarbon transportation;
refining (reactors, conduits, condensers);
petro chemical (reactors, conduits, condensers);
chemical (reactors, conduits, condensers);
food storage and processing;
heat exchangers;
cryogenic systems;
biosensors;
chemical sensors;
power generation (reciprocal, turbine, hydro, fuel cells);
vapor detection (humidity, fumes);
medical (device, pharma);
laboratory (automated, hand-held);
printing (industrial printers, deskjet);
manufacturing (paints, inks);
manufacturing equipment monitoring (CNC equipment lubricant, extrusion polymer monitoring);
environmental hazard sampling and monitoring;
homeland security; and
petrochemical transportation.

The inventions can also be advantageously used, for example, to monitor fluids in any of the following fluidic systems:

engines (reciprocal, turbine, electric);
brakes (automotive, industrial);
transmissions (hydraulic, gear);
heat exchangers (radiators, HVAC&R, coolers, chillers);
fuel storage and transmission;
pipelines;

storage tanks;
HVAC&R systems;
compressors (air, gas);
vacuum pumps;
gear boxes;
dewars;
buildings (atmospheric in buildings and houses . . . aka humidity sensor);
mammalian body (veins, lungs, gut);
wells (oil, gas, water);
printing press;
turbines; and
lubrication systems.

The inventions can also be advantageously used, for example, to monitor fluids in any of the following fluids:
oils, greases, hydraulics (synthetics and HC);
gases (reactor feeds, HC's, inorganics including cryo's);
heat exchanger fluid (water, glycol, "downtherms", refrigerants);
crude oil;
fuel (gasoline, diesel, biodiesel, ethanol, methanol, hydrogen);
mammalian (blood, urine, vaginal);
food (batter, oils, greases, gels, pastries, alcohols);
solvents (laboratory, industrial, home);
cleaners (windshield washer fluid, etc.);
ink;
fluidized beds;
ambient air;
exhaust gases;
hydrogen; and
inert gases.

Specific End-Use Applications

The methods and systems and apparatus of the invention can be used to monitor fluidic systems for various purposes. The inventions can be advantageously used, for example, to monitor fluids in any of the field applications and/or fluidic systems and/or fluid types as shown in FIGS. 11A through 11C.

Particularly preferred applications involve heating, ventilating, air conditioning and refrigeration (HVAC&R) applications. In these applications, the fluidic systems can include circulating fluids such as circulating refrigerants, circulating coolants, circulating lubricants and circulating oils. In general, many fluids used in HVAC&R fluidic systems can be collectively referred to as thermal change fluids—fluids which have a thermal property change within the fluidic system, for example, typically within each cycle of a fluidic system, including for example, changes due to one or more unit operations (e.g., fluid compression, fluid expansion, heat transfer, etc.). Hence, a thermal change fluid can include: refrigerants, coolants, lubricants, oils and mixtures thereof. For example, coolant being compressed in an HVAC&R fluidic system can include compressor lubricant or oil. Also, the engines driving such compressors or other devise can have their own isolated fluidic systems (e.g., circulating oil fluidic system).

Transportation vehicles are also particularly preferred.

Fluidic systems in heavy machinery, such as engines and compressors are also particularly preferred.

EXAMPLE

A sensor comprising a flexural resonator having internal, embedded electrodes was used to measure three fluids—air, deionized water and saturated salt water. This example demonstrated that the flexural resonator sensor was effective in sensing diverse fluids, including both gaseous and liquid fluids and including both non-ionic and ionic (e.g., conducting) fluids.

A tuning fork resonator having internal, embedded electrodes was manufactured using microfabrication protocols, substantially as disclosed above in paragraphs [0045] to [0051] hereof.

Figure 6A:
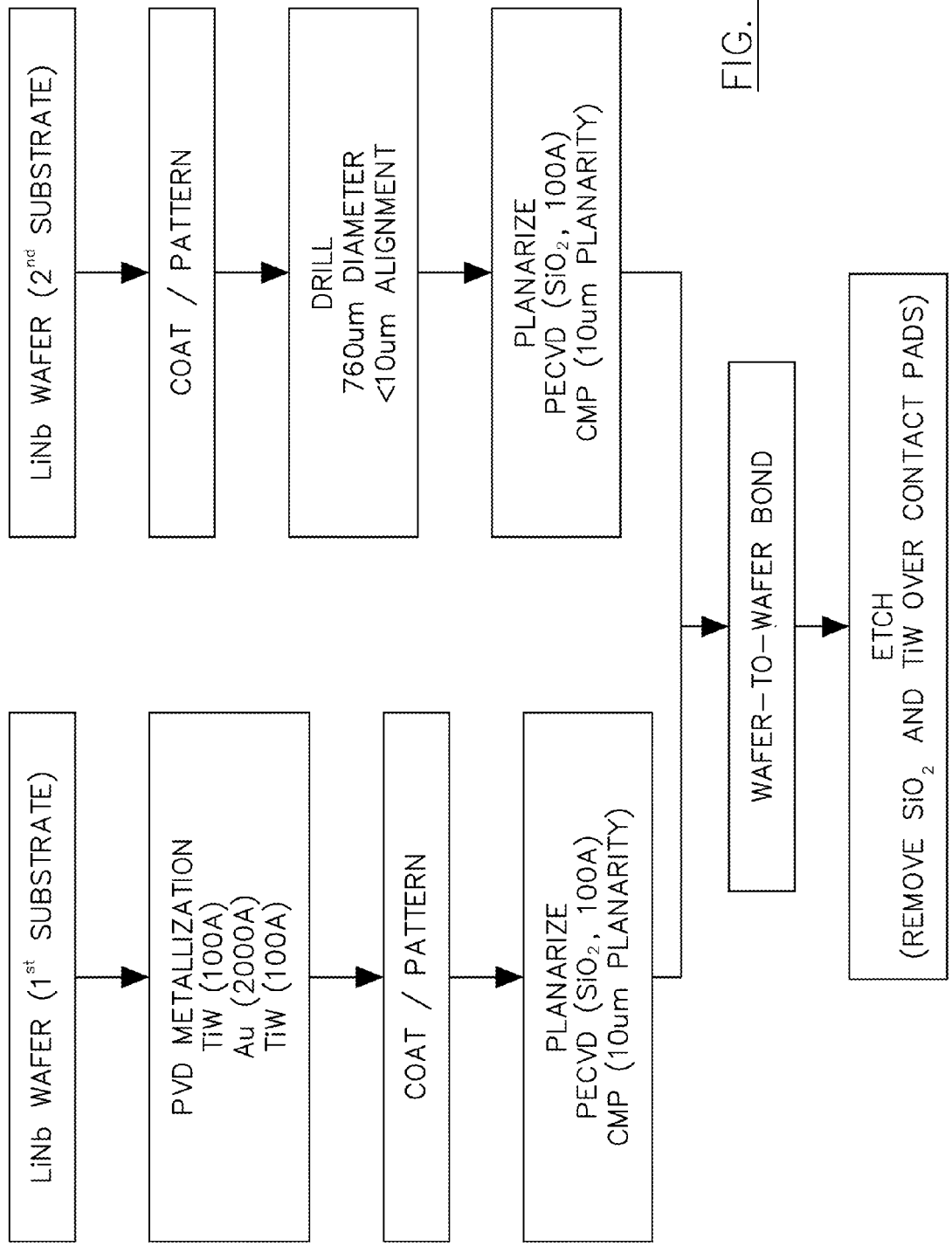
FIGS. 6A and 6B are a schematic block diagram (FIG. 6A) depicting a fabrication protocol for an embedded electrode tuning fork resonator used in Example 1, and a graph (FIG. 6B) showing data representing the response of a tuning fork resonator having embedded electrodes as used in Example 1, the response depicted therein as superimposed plots with data overlaid from each of three separate experimental runs, including where the sensing portion of the tuning fork resonator was contacted (i) in one experiment, with air at room temperature and atmospheric pressure (shown with triangle-shaped data points), (ii) in another experiment, with deionized water at room temperature and atmospheric pressure (shown with circle-shaped data points), and (iii) in a further experiment, with a saturated salt water solution at room temperature and atmospheric pressure (shown with square-shaped data points).

Briefly, with reference to FIG. 6A, to prepare a first subassembly, pairs of gold electrodes were patterned onto a first surface of a first lithium niobate substrate (~0.5 mm) using photolithographic patterning and thin-film physical vapor deposition (e.g., sputtering) techniques. The deposition process included, sequentially, TiW (100 Å) as an underlying adhesion promoter, Au (2000 Å) as the electrode, and TiW (100 Å) as an overlying adhesion promoter. The electrodes were configured substantially as shown in FIG. 1C. This configuration allowed the tuning fork tines to move, during operation within the sensor upon electronic simulation, in an opposing symmetrical manner within a common plane, as shown in FIG. 7B. The overall pattern on the lithium niobate substrate was substantially as shown in FIG. 2B. A silica oxide (100 Å) overcoating layer was applied over the patterned gold electrodes using plasma enhanced chemical vapor deposition (PECVD), and the oxide layer of this first subassembly was then planarized and polished using chemical mechanical polishing (CMP) to form thin oxide overlayer.

A second subassembly comprising a second lithium niobate substrate with a thin silicon oxide overlayer was also prepared. Briefly, referring again to FIG. 6A, a lithium niobate substrate (~0.5 mm) was provided with a patterned protective overcoat and then drilled using abrasive drilling techniques to form a plurality of apertures (760 mm diameter) therein, in an patterned arrangement that corresponded to the patterned arrangement of the electrode contact pads formed in connection with the first subassembly (For this example, the alignment specification was less than 10 um). A silicon oxide (100 Å) overcoating layer was then applied over drilled LiNb substrate using plasma enhanced chemical vapor deposition (PECVD), and the oxide layer of the second subassembly was then planarized and polished using chemical mechanical polishing (CMP) to form thin oxide overlayer.

The first and second subassemblies were then bonded, specifically with the planarized, polished oxide surface of the first subassembly bonded to the planarized, polished oxide surface of the second subassembly. The subassemblies were bonded using commercial techniques (Ziptronics, Inc., CA). The resulting assembled composite wafer included embedded patterned tuning fork electrodes for a large number of tuning forks (See, for example, FIG. 3).

The wafers were diced after bonding, using a standard wafer dicing saw (American Precision Dicing, CA) to form the piezoelectric tuning fork resonator. (See, for example, FIG. 4).

In the prototype embodiment used in this example, conductive electrical leads were positioned in the apertures and bonded to the contact pads of the gold internal electrodes using silver epoxy. A protective overcoat of non-conductive epoxy was applied over the electrical connections within the apertures. The electrical leads electrically connected the internal electrodes of the tuning fork resonator with a printed circuit electronics board. The printed circuit electronics board was connected to a network analyzer (Hewlett Packard, CA). The network analyzer was configured as known in the art to generate an electronic input stimulus that included a waveform of varying frequency over a predetermined frequency range, and was further configured to receive a response signal representing the response of the tuning fork resonator.

In one experimental run, the sensing portion of the tuning fork resonator was contacted with air at room temperature and atmospheric pressure. In another experimental run, the sensing portion of the tuning fork resonator was contacted with deionized water at room temperature and atmospheric pressure. In a further experimental run, the sensing portion of the tuning fork resonator was contacted with a saturated salt water solution at room temperature and atmospheric pressure.

Figure 6B:
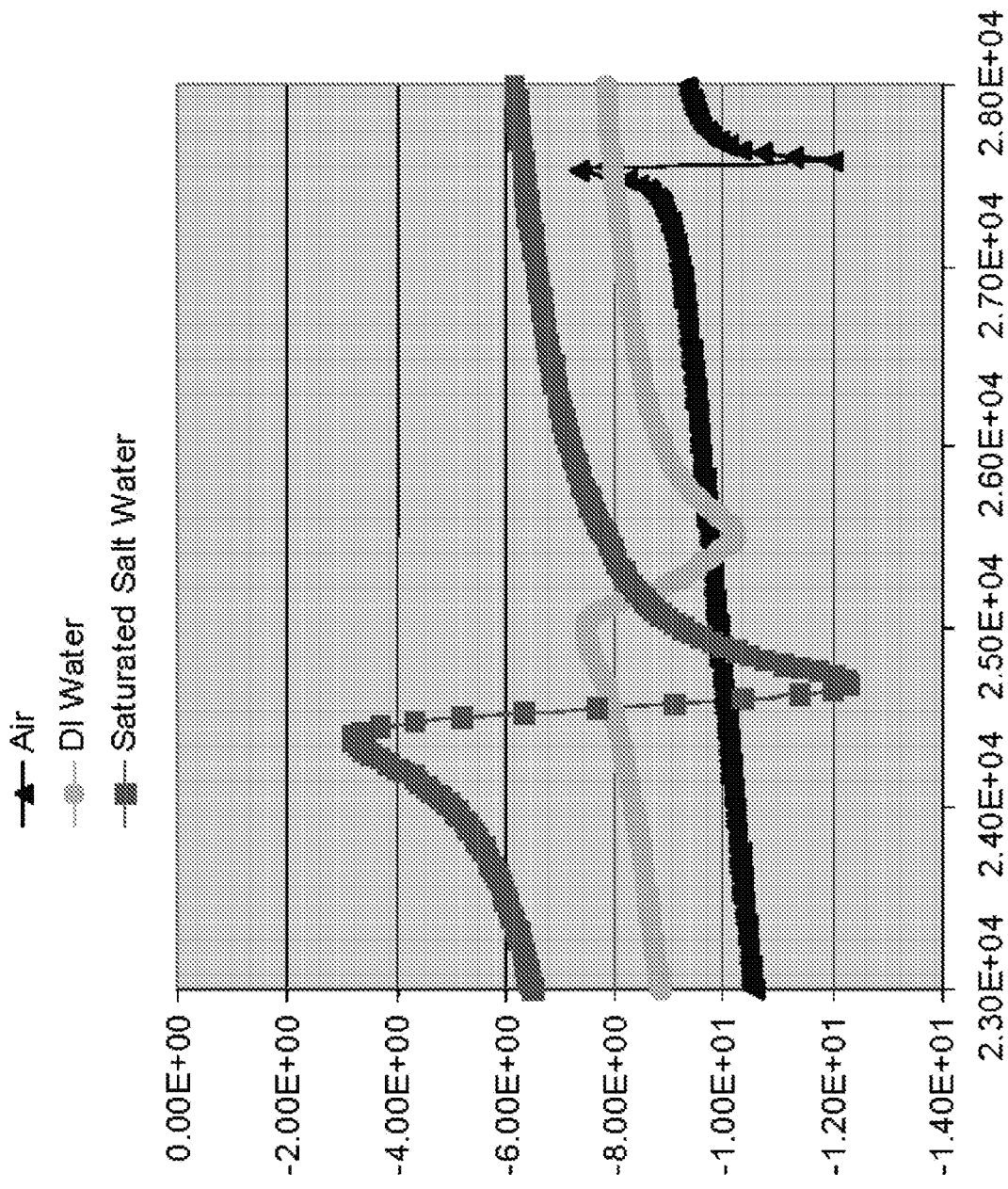

The results from the experimental runs are shown in FIG. 6B, depicted therein as superimposed plots of sensor response signal (amplitude, dB) as measured by the network analyzer (y-axis, as shown) versus frequency (Hz) (x-axis, as shown) with the data overlaid from each of the three described experimental runs. The data showed differences in resonance frequencies and amplitudes corresponding to the differences in fluid properties for the three different fluid types tested. Significantly, the response signal associated with the saturated salt water solution demonstrated that the sensor of the invention, having embedded electrodes, could be suitably applied for determining fluid properties of conducting, ionic liquids. In contradistinction, a typical mechanical resonator having electrodes exposed on the exposed surface of the sensing portion of the resonator would have been shorted out in salt water solution.

Moreover, although a conducting external electrode (e.g., gold external electrode) was not employed in connection with the sensor embodiment used for this example, it is expected that use of such an external electrode would have a beneficial effect, especially for sensing ionic fluids. Specifically, without being bound by theory, the external electrode is expected to act substantially as a faraday cage, to effectively operate as a capacitive shield, and/or to substantially contain the electric field within the piezoelectric tuning fork resonator (i.e., to minimize the extent to which the electrical field within the piezoelectric tuning fork resonator is coupled to the fluid under test during operation of the sensor). Preferably during operation, the gold external electrode would be in contact only with the fluid under test.

In light of the detailed description of the invention and the example presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

We claim:

1. A fluid sensor comprising a tuning fork resonator, the tuning fork resonator comprising a piezoelectric material, and an electrode comprising at least a first surface and a second surface, at least a portion of the electrode being embedded in the piezoelectric material such that the piezoelectric material is disposed over and in electronic association with the first surface of the electrode, and such that the piezoelectric material is disposed over and in electronic association with the second surface of the electrode, wherein the piezoelectric material comprises at least one of quartz and lithium niobate, wherein the tuning fork resonator comprises a sensing portion having an exposed surface for contacting a fluid, and wherein at least a portion of the electrode is embedded in the sensing portion.

2. The fluid sensor of claim 1 wherein the piezoelectric material comprises a first piezoelectric material disposed over and electronically associated with the first surface of the electrode, and a second piezoelectric material disposed over and electronically associated with the second surface of the electrode.

3. The fluid sensor of claim 2 wherein the first piezoelectric material and the second piezoelectric material are the same type of piezoelectric material.

4. The fluid sensor of claim 2 wherein the first piezoelectric material and the second piezoelectric material are different types of piezoelectric material.

5. The fluid sensor of claim 2 wherein the first piezoelectric material and the second piezoelectric material are physically contiguous.

6. The fluid sensor of claim 2 wherein the first piezoelectric material and the second piezoelectric material are physically discrete.

7. The fluid sensor of claim 2 wherein the first piezoelectric material contacts the first surface of the electrode.

8. The fluid sensor of claim 2 wherein the second piezoelectric material has a thickness, the tuning fork resonator further comprising an intermediate material disposed between the second piezoelectric material and the second surface of the electrode, the intermediate material having a thickness that is less than the thickness of the second piezoelectric material.

9. The fluid sensor of claim 1 further comprising an intermediate material disposed between the piezoelectric material and at least one surface of the electrode.

10. The fluid sensor of claim 1 wherein the second surface of the electrode substantially geometrically opposes the first surface of the electrode.

11. The fluid sensor of claim 1 wherein the first surface of the electrode is a first major surface of the electrode, the second surface of the electrode is a second major surface of the electrode, the first and second major surfaces being substantially parallel to and being substantially geometrically opposed to each other, the electrode further comprising a third minor surface and a fourth minor surface, the third and fourth minor surfaces being substantially parallel to and being substantially geometrically opposed to each other.

12. The fluid sensor of claim 11 wherein the piezoelectric material is disposed adjacent to and in electronic association with each of the third minor surface and the fourth minor surface of the electrode.

13. The fluid sensor of claim 11 further comprising a bondable material disposed adjacent to and in contact with each of the third minor surface and the fourth minor surface of the electrode.

14. The fluid sensor of claim 11 further comprising an insulating material disposed adjacent to and in contact with each of the third minor surface and the fourth minor surface of the electrode.

15. The fluid sensor of claim 1 wherein the entire operative electrode is embedded in the piezoelectric material.

16. An apparatus comprising a flexural resonator, the flexural resonator comprising a sensing portion having an exposed surface for contacting a fluid, a piezoelectric material, and at a least one pair of electrodes configured for generating an electric field between them within the piezoelectric material, the at least one pair of electrodes comprising an internal first electrode, at least a portion of the first electrode being embedded in the piezoelectric material such that substantially opposing surfaces of the first electrode are in electronic association with the piezoelectric material, and an external second electrode, at least a portion of the second electrode having a first surface and a second surface, the first surface thereof being in electronic association with the piezoelectric material, the exposed surface of the sensing portion consisting essentially of the second surface of the second electrode.

17. An apparatus comprising a flexural resonator, the flexural resonator comprising a sensing portion having an exposed surface for contacting a fluid, a piezoelectric material, and at a least one pair of electrodes configured for generating an electric field between them within the piezoelectric material, the at least one pair of electrodes comprising an internal first electrode, at least a portion of the first electrode being embedded in the piezoelectric material such that substantially opposing surfaces of the first electrode are in electronic association with the piezoelectric material, and an external second electrode, at least a portion of the second electrode having a first surface in electronic association with the piezoelectric material, the first and second electrodes being configured such that upon activation, (i) the electric field generated between therebetween is substantially contained within the piezoelectric material, and (ii) the piezoelectric material resonates.

18. The apparatus of claim 16 or 17 wherein the second electrode is grounded.

19. The apparatus of claim 16 or 17 wherein the flexural resonator comprises a tuning fork.

20. The apparatus of any of claims 1, 16, or 17 further comprising a temperature sensing element having a sensing surface proximate to a sensing portion of the resonator.

21. A method of using the apparatus of one of claims 1, 16, or 17, the method comprising contacting a sensing portion of the resonator of the apparatus with a fluid, stimulating the fluid-contacted resonator, and monitoring a response of the resonator.

22. The method of claim 21 further comprising determining at least one property of the fluid, the at least one property being determined by correlating the response of the resonator with a property of the fluid in contact therewith.

23. The method of claim 21 wherein the fluid-contacted resonator is stimulated to generate a signal associated with a response of the resonator, and the response of the resonator is monitored by a method comprising communicating the generated signal over a communication path to an electrical circuit comprising signal processing circuitry or data retrieval circuitry.

24. The method of claim 23 wherein the resonator is stimulated with an electronic stimulus.

25. The method of claim 23 wherein the flexural resonator comprises a tuning fork.

26. A fluid sensor comprising a flexural resonator, the flexural resonator comprising a piezoelectric material, and an electrode comprising at least a first surface and a second surface, at least a portion of the electrode being embedded in the piezoelectric material such that the piezoelectric material is disposed over and in electronic association with the first surface of the electrode, and such that the piezoelectric material is disposed over and in electronic association with the second surface of the electrode,
wherein the piezoelectric material comprises at least one of quartz and lithium niobate,
wherein the piezoelectric material comprises a first piezoelectric material disposed over and electronically associated with the first surface of the electrode and a second piezoelectric material disposed over and electronically associated with the second surface of the electrode, and
wherein the second piezoelectric material has a thickness, the flexural resonator further comprising an intermediate material disposed between the second piezoelectric material and the second surface of the electrode, the intermediate material having a thickness that is less than the thickness of the second piezoelectric material.

27. A fluid sensor as set forth in claim 26 wherein the flexural resonator comprises a tuning fork.

28. A fluid sensor comprising a flexural resonator, the flexural resonator comprising a piezoelectric material, an electrode comprising at least a first surface and a second surface, and an intermediate material, at least a portion of the electrode being embedded in the piezoelectric material such that the piezoelectric material is disposed over and in electronic association with the first surface of the electrode and such that the piezoelectric material is disposed over and in electronic association with the second surface of the electrode, the intermediate material being disposed between the piezoelectric material and at least one surface of the electrode, wherein the piezoelectric material comprises at least one of quartz and lithium niobate.

29. A fluid sensor as set forth in claim 28 wherein the flexural resonator comprises a tuning fork.

* * * * *